United States Patent [19]

Masilamani et al.

[11] Patent Number: 5,162,525
[45] Date of Patent: Nov. 10, 1992

[54] FLUOROGENIC AND CHROMOGENIC THREE-DIMENSIONAL IONOPHORES AS SELECTIVE REAGENTS FOR DETECTING IONS IN BIOLOGICAL FLUIDS

[75] Inventors: Davakaran Masilamani, Morristown; Mariann E. Lucas, Netcong; George S. Hammond, Madison, all of N.J.

[73] Assignee: Allied-Signal Inc., Morristownship, Morris, N.J.

[21] Appl. No.: 80,721

[22] Filed: Jul. 31, 1987

[51] Int. Cl.$^5$ .................. C07D 419/02; C07D 321/00; G01N 33/20
[52] U.S. Cl. ..................... 540/468; 540/469; 540/472; 509/200; 509/348; 509/349; 509/350; 509/351; 509/352; 436/74
[58] Field of Search .................. 436/74; 540/468, 469, 540/477; 549/200, 348, 349, 350, 351, 352; 546/337

[56] References Cited

U.S. PATENT DOCUMENTS 4,645,744  2/1987  Charlton ............................. 436/74
4,808,539  2/1989  Chapiteau .......................... 436/74

OTHER PUBLICATIONS

H. G. Lohr et al. "Chomo and Fluoroionephores..." Acct. Chem. Res. 18 65–72 (1985).
K. W. Street et al. "A New Metal Sensitive Fluorescence Reagent" Analytic Ltrs., 19 (7&8), 735–745 (1986).
A. P. de Silva et al. "Fluorescent Signalling Crown Ethers; 'Switching on' of Fluorescence..." J. Chem. Soc., Chem. Commun, 1986, pp. 1709–1710.
J. P. Konopelski et al. "Synthesis, Cation Binding, and Photophysical Properties..." J. Chem. Soc. Chem. Commun., 1985 pp. 433–435.
J. M. Lehn "Cryptates: Macropolycyclic Inclusion Complexes" Pure & Appl. Chem., vol. 49, pp. 857–870 Pergamon Press.
R. L. Muray "Principles of Analysis and Current Usage" Toxicology and Therapeutic Drug Monitoring (DMTC) pp. 1377–1379.
H-G Lohr et al. "Chromo- And Fluoroionophores, A New Class of Dye Reagents" Acc. Chem. Res. 1985, 18, 65–72.
M. Takagi et al. "Crown Compounds as Alkali and Alkaline Earth Metal Ion . . . " Property of Chemical Abstract Service pp. 39-65.
H. Nishida et al., "Fluorescent Crown Ether Reagent for Alkali and Alkaline Earth Metal Ions" Chemistry Ltrs., pp: 1853–1854, 1982.

Primary Examiner—C. Warren Ivy
Assistant Examiner—Celia Chang
Attorney, Agent, or Firm—D. L. Webster; G. H. Fuchs; R. C. Stewart, II

[57] ABSTRACT

Novel fluorogenic and chromogenic three-dimensional ionophores are provided which selectively bond ions such as potassium, sodium, and lithium, even in neutral aqueous or alcohol media. The novel ionophores comprse an "ion-recognizing system" fused to a "signal-moiety" through one or more heteroatoms having a non-bonded electron pair. The signal-moieties are selected from the group consisting of fused ring heterocyclics, fused aromatics, and substituted aromatics having at least one nitro or azo moiety. The ion-recognizing system is a three-dimensional cryptand. The ionophores are ideal for the selective and direct termination of ions in biological or environmental samples and the like.

11 Claims, 9 Drawing Sheets

FLUOROGENIC AND CHROMOGENIC THREE-DIMENSIONAL IONOPHORES AS SELECTIVE REAGENTS FOR DETECTING IONS IN BIOLOGICAL FLUIDS

FIELD OF THE INVENTION

Novel ionophores have been synthesized which selectively bind ions such as potassium, sodium, and lithium, even in neutral aqueous and alcoholic media and respond to such binding by fluorescence quenching or enhancement, or by changing color. These ionophores are ideal for the selective and direct determination of ions in biological or environmental samples and the like. The ionophores are also suitable for incorporation into fiber optic-based sensors for the continuous in vivo or in vitro monitoring of metal ions in blood or other biological fluids.

BACKGROUND OF THE INVENTION

Chromogenic ionophores (or ionophore dyes) are a class of color-responsive reagents for detecting alkali and alkaline earth metal ions. In these reagents, a size-specific ionophore group (the ion recognizing ionophore) is fused to an aromatic ring which in turn is functionalized with a chromophore such as an azo, or picrylamino group. Chromogenic ionophores have been extensively studied (see H-G. Lohr and F. Vogtle. "Chromo and Fluoroionophores. A New Class of Dye Reagents." Acc. Chem. Res. 1985. 18, 65-72; M. Tagaji; and K. Uneo, "Crown Compounds as Alkali and Alkaline Earth Metal Ion Selective Chromogenic Reagents." Top. Curr. Chem. 1984 121, 39-65). There are two classes of chromogenic ionophores, those that show a pH-dependent response and those that function at neutral pH. The former class of ionophores shows dramatic changes in color. However, the colored form is usually detected in organic solvents and hence an extraction step is essential in addition to adjustment of the pH of the system. Chromoionophores presently known to the art, that function at neutral pH, have yet to demonstrate a sufficient change in color. Without an easily detectable change in color, these chromoionophores cannot be useful as analytical reagents and the like.

A second type of ionophore is the "fluoroionophore." The measurement of fluorescence quenching or enhanced fluorescence emission when metal ions are bound to these fluorogenic ionophores is more accurate than measurements based on chromogenic phenomena. This is because fluorescence measurements are made against a dark background, whereas chromogenic methods require detection of absorption maxima or charges in absorption coefficients. Among the fluorogenic ionophores reported in the literature are those described by Nishida, et al. "Fluorescent Crown Ether Reagent For Alkali and Alkaline Earth Metal Ions," *Chem. Lett., pp.* 1853-1854, (1982), by Kenneth W. Street, Jr. and Shelly A. Kraus in "A New Metal Sensitive Fluorescence Reagent," *Anal. Lett.,* 19 (7 and 8), 735-745 (1986), and by A. P. deSilva et al., "Fluorescent Signaling Crown Ethers: 'Switching On' of Fluorescence by Alkali Metal Ion Recognition and Binding in situ" J. Chem. Soc., Chem. Commun. 1986, 1709-10. However, all the above ionophores suffer from a disadvantage in that they are pH dependent, and can function only at a pH much higher than that of normal body fluid, and hence cannot be used for in vivo applications.

SUMMARY OF THE INVENTION

The present invention provides a novel ionophore comprising an "ion-recognizing system" fused to a "signal moiety" through one or more heteroatoms having a non-bonded electron pair said ionophore having the General Structural Formula:

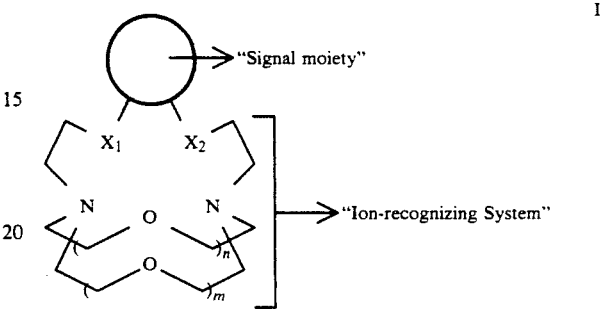

wherein said "signal moiety" is selected from the group consisting of fused ring heterocyclics, fused aromatics, and substituted aromatics having at least one nitro or azo moiety; and wherein said "ion recognizing system" is a three-dimensional cryptand wherein $X_1$ and $X_2$ of said three dimensional cryptand are the same or different and are heteroatoms selected from the group consisting of oxygen (O) nitrogen (N), sulfur (S), phosphorous (P), and selenium (Se); and the repeating units m and n are the same or different and are integers from about 0-12.

In the preferred embodiments, the signal moiety is selected from the group consisting of coumarins, anthracenes, azo aromatics, nitro aromatics, particularly nitroaniline dyes; and said cryptand contains heteroatoms selected from the group consisting of O, N, S and P.

The preferred heteroatoms in the cryptand moiety as depicted in General Structure 1 are nitrogen (N) and oxygen (O); and the repeating units n and m are the same or different and are preferably integers from about 1-3. Further, these ionophores function at neutral pH in aqueous or alcoholic media.

DETAILED DESCRIPTION OF THE INVENTION

Figure 1:
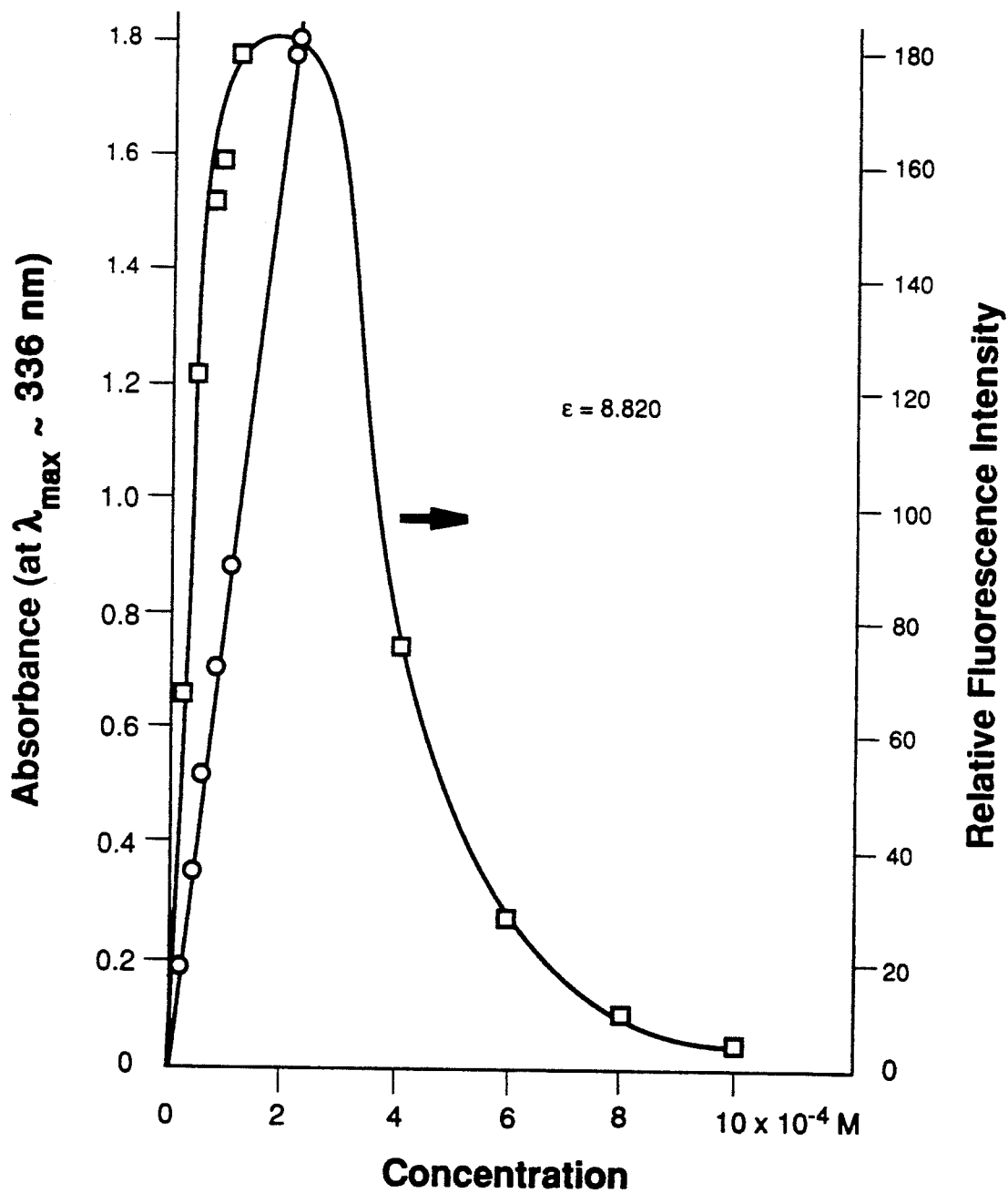
FIG. 1 depicts a graph of absorbance values and relative fluorescence intensity versus concentration of a representative reagent ionophore.

The selective reagent ionophores of the present invention comprise two moieties, a "signal moiety" and an ionophoric three-dimensional cryptand moiety, the latter capable of complexing with various metal ions. In this sense, the three-dimensional cryptand forms the "ion-recognizing system." (See General Structure 1).

The "signal moiety" in the compounds of the invention is a chemical moiety bound to the "ion-recognizing" cryptand and can exhibit a change in optical properties upon complexing of a metal ion with the cryptand moiety. This change in optical properties may be evidenced colorimetrically when binding of the metal ion causes a shift in absorption maximum, or fluorometrically when there is a change in the fluoroscence.

The signal moiety is considered chromogenic when the change in optical properties is a colorimetric one. This change may be detected visibly or through the use of spectrophotometric or reflectance measurements. Of the preferred azo and nitro aromatics, and particularly nitroaniline dyes, may be mentioned 4-nitro phenyl azo, trinitro azo, 2,4-dinitro azo, picrylamino, 2,6-dinitro-4-trifluoromethylanilino, 4-nitro sulfonamide and the like. Representative chromogenic signal moieties in the reagents of the invention are shown as follows, fused to representative cryptands:

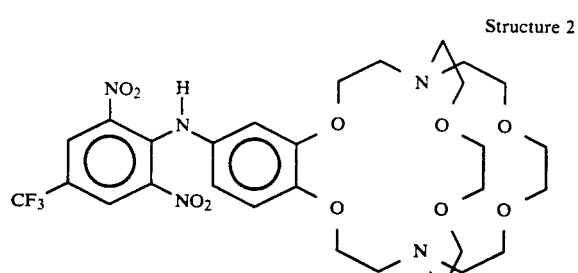

Structure 2

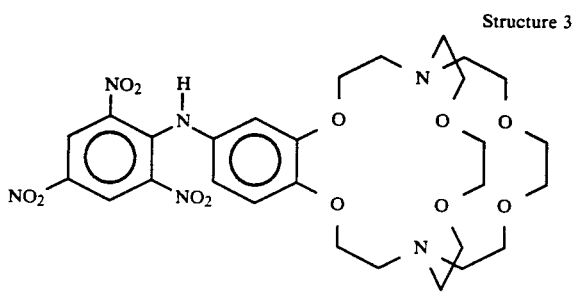

Structure 3

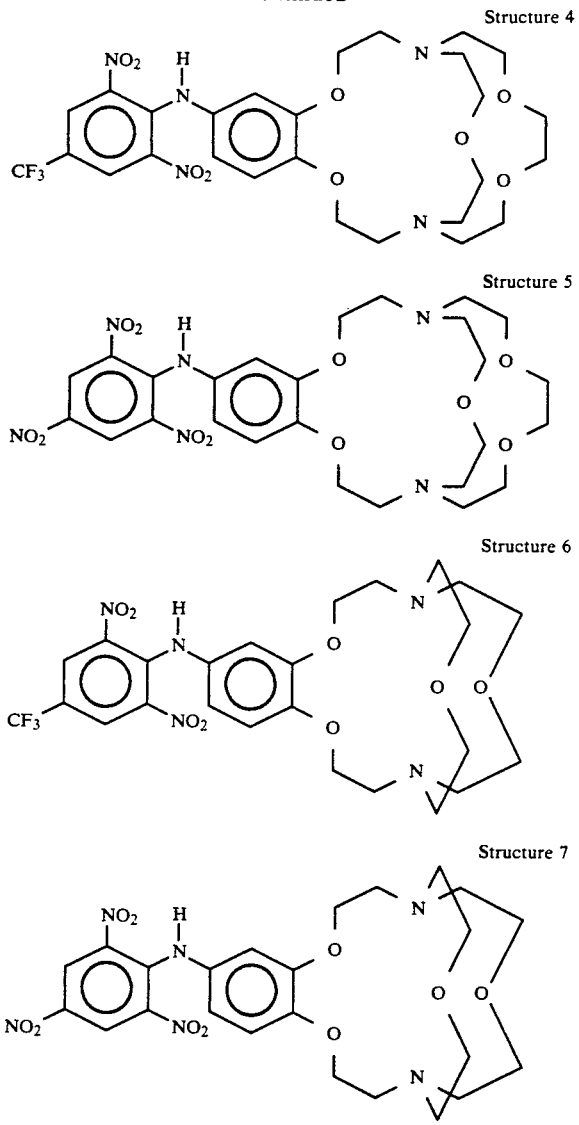

Ionophores, such as those depicted in Structures 2 and 3 are selective for potassium ion. They are typically yellow in color, and may become red on binding potassium ion. The same color change is anticipated for ionophores shown in Structures 4 and 5 for sodium ion and those shown in Structures 6 and 7 for lithium ion.

The change in optical properties is evidenced fluorometrically when binding of the metal ion causes quenching or enhancement of fluorescence. Fluorescence measurements are preferred to absorption measurements since light intensities are measured against a dark background. Additionally, between fluorescence quenching and fluorescence emission, the latter is preferred, since in this measurement, signal to noise ratio is minimized, particularly at higher concentrations of metal ions. Thus, the signal moiety in the fluorogenic three-dimensional cryptands of the invention is designed to absorb light, preferably above 300 nm. and re-emit the absorbed light energy as fluorescence. The signal moiety contains a chromophoric group or several chromophoric groups, capable of efficient absorption of light energy. Of the preferred chromophores for fluorescent emission are those having carbonyl groups, carbon-carbon double bonds, and aromatic rings. In the preferred embodiments of the reagent ionophores of the invention, fused rings such as naphthalenes, anthracenes, benzofurans, benzodiazines, benztrioxazines, benzotriazepines, pyrenes, coumarins (or 1,2-benzopyrones) and the like are used as the fluorescent signal moiety. In the particularly preferred embodiments, a coumarin is the signal moiety, a typical structure being depicted below.

Coumarin (1,2-Benzopyrone)     Structure 8

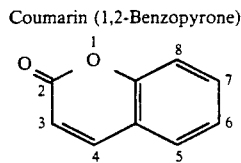

Of the preferred coumarins are those having one or more substitutions at positions 3 4 5, 6 or 8. Illustrative substituents may be hydrogen, hydrocarbons, esters acids, fluorinated hydrocarbons, aromatic groups, ethers, thiols, thioethers or various combinations of these groups, and the like. Structure 9 (a) and (b) is representative (substituents indicated by $R_1$-$R_4$):

Structure 9

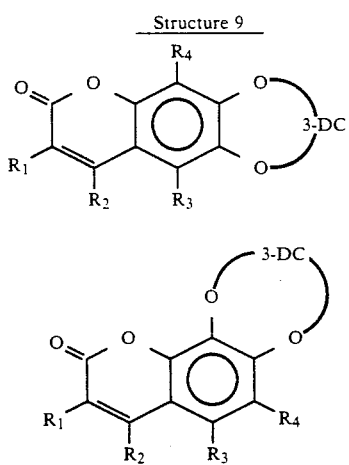

wherein $R_1$, $R_2$, $R_3$, $R_4$ are the same or different and are H, hydroxy, amine, alky, aryl, fluorocarbon, ester, acid, ether, thiol, or thioether (and 3DC=three-dimensional cryptand).

In the more preferred embodiments, substituting the hydrogen at position 7 in the coumarin ring with a heteroatom with lone pairs of electrons has been discovered to enhance the quantum yield of fluorescence. While the present inventors do not wish to be bound by theory, this may be due to the stabilization of the dipolar form, as illustrated in Structures 10 and 11 for oxygen atom which increases the transition moment of the lowest energy electronic excitation of the molecule:

Structure 10

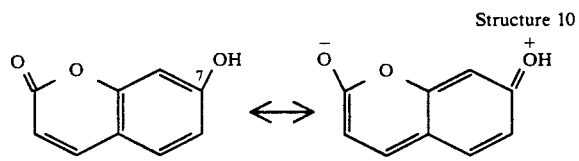

-continued

Structure 11

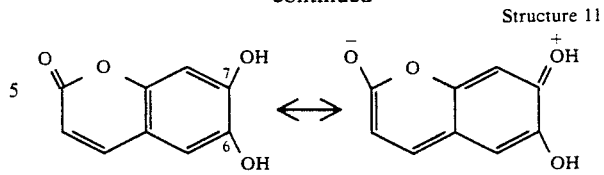

A particularly preferred reagent ionophore of the invention comprises 4-methylcoumarin fused to a three-dimensional cryptand through positions 6 and 7 or 7 and 8. The fusion may be through two heteroatoms such as P, S, N, O or Se, which may be the same or different at these positions. However, it is particularly preferred that O be the heteroatom at both of the positions. Structures 12 and 13 depict certain preferred embodiments.

Structure 12

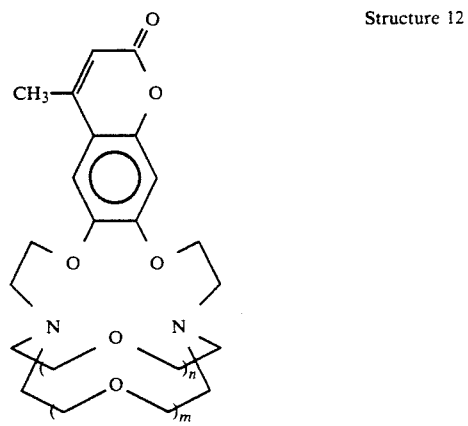

Structure 13

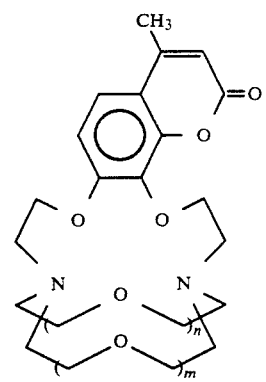

Although the present inventors do not wish to be bound by scientific theory, or in any other way be limited thereby, they have discovered that when irradiated, compounds such as those shown in Structures 12 and 13 may be excited to polar states. It has been postulated that when the metal ion binds to the ionophore, it drains the electrons from the heteroatoms of the ionophore and thus causes electronic perturbations in these heteroatoms, i.e.: the electrons flow from the heteroatoms to the newly complexed metal ion. In the compounds of the present invention, one of the heteroatoms is a source of electrons transferred to the remote carbonyl oxygen in the process of optical excitation. The molecule as a whole responds to the presence of a selectively bound metal ion causing a change in fluorescence emission. This change is used to deduce the presence of and, if desired, to quantitate the amount of the target metal ion that has been drawn from its surrounding medium to bind to the ionophore. Thus, the signal moiety serves as an optical transducer for measuring the ion-recognizing capability of the ionophore.

The ion-recognizing moiety of the novel compounds of the invention is a three-dimensional cryptand, that can vary widely with respect to its cavity dimensions. By the term cavity is meant the three-dimensional spherical space available for metal ion binding within the cryptand. In general, cavity dimensions should be approximately the size of the ionic diameter of the ion it is desired to accomodate. It is thus preferred that the cavity dimensions not be substantially larger or smaller than the ionic diameter. In this sense, it is preferred that the cavity dimensions not vary from the ionic diameter of the ion by more than about ±0.8Å, preferably not more than about ±0.5Å, and most preferably not more than about ±0.2Å. It should be appreciated that the cryptands are selected according to their cavity measurements for detection of particular ions. For example, lithium ion has an ionic diameter of 1.2Å, sodium ion, approximately 1.9Å, and potassium ion approximately 2.66Å. Thus,. the cavity diameter can be varied from about 1.3Å to about 3.0Å in order to selectively accommodate these particular ions. One skilled in the art will understand that the cavity size can be progressively increased by increasing the number of bridging ethoxy groups (for example increase the number of repeating units n and m in Structures 12 and 13 from 0 to 12).

From the work of J. M. Lehn ("Cryptates: Macropolycyclic Inclusion Complexes," pure & Appl. Chem., 1977, 49, 857–870) it is known that 211, 221 and 222 ctyptands (Structures 14. 15 and 16)

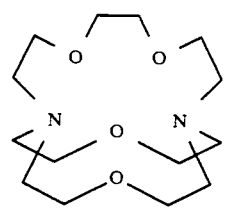

Structure 14

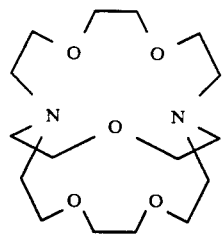

Structure 15

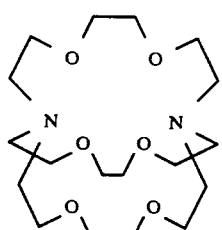

Structure 16 with a cavity diameter of 1.6Å, 2.2Å and 2.8Å respectively, are selective for binding lithium, sodium, and potassium ions, respectively, and thus are particularly preferred as the ion-recognizing moieties of the reagents of this invention.

In the preparation of the compounds of the invention, the signal group is attached to two pendant reactive groups. Of these pendant reactive groups may be mentioned 2-hydroxyethoxy, 2-chloroethoxy, 2-iodoethoxy, 3-hydroxypropoxy, and the corresponding chloro and iodo analogues of these compounds, and the like. This reaction may be carried out by conventional methods such as nucleophilic substitution reactions.

For example, these two pendant groups may be attached simultaneously to the two nitrogens of a two-dimensional diazacrown ether to produce the three-dimensional cryptand. Of the two-dimensional diazacrown ethers useful in this synthesis may be mentioned 1.10-diaza-18-crown-6. 1.7-diaza-15-crown-5, 1,7-diaza-12-crown-4, 1.10-diaza-21-crown-7, 1,13-diaza-24-crown-6, 1,13-diaza-27-crown-7, 1.16-diaza-30-crown-8, and 1,4-diaza-9-crown-3. Such crown ethers may be obtained commercially or first synthesized de novo according to procedures set forth in published literature. It should be appreciated that the size of the two dimensional diaza-crown ether will, to a great extent, govern the cavity size of the resulting three-dimensional cryptand.

In the preferred syntheses of the preferred ionophores, a fluorescing signal moiety such as 4-methylcoumarin is attached to two 2-hydroxy-ethoxy pendant groups at positions 6 and 7, by reacting commercially available 4-methylesculetin (6.7-dihydroxy-4-methylcoumarin) with two mole equivalents of 2-bromoethanol. The resulting compound is chlorinated and the chlorines displaced by iodines to form 6,7-di(2'-iodoethoxy)-4- methylcoumarin. This compound may then be preferably reacted with diazacrown ethers such as 1.10-diaza-18-crown-6, 1,7-diaza-15-crown-5 or 1,7-diaza-12-crown-4, to obtain 6,7-(4-methyl) coumaro[222] cryptand, the corresponding [221] and [211] cryptands respectively. 1,10-diaza-18-crown-6 and 1,7-diaza-15-crown-5 are commercially available, and 1,7-diaza-12-crown-4 may be synthesized according to the procedure of J. M. Lehn (U.S. Pat. No. 3,888,877, Jun. 10, 1975).

In its broadest aspect, the method of using the compounds of the invention as reagent ionophores to detect ions may be carried out by simply contacting the ionophore with the sample, which may contain the target ions. Detection of ions using the ionophores of the invention may take place in liquid media varying widely in composition. For example, a pure alcohol medium, a pure aqueous medium, or a mixture of both is suitable. However, if the reagent ionophore is used in a liquid form, it is preferably in a solution medium that is compatible with the sample under analysis.

It should be appreciated that the present reagent ionophores, especially the fluorogenic ionophores, do function quite well in neutral or basic pH media. Thus, monitoring of crude biological systems is possible with these reagents. Crude biological, physiological, environmental samples and the like may be assayed in their natural states for ion content, preferably after minimum sample preparation is performed, such as freeing the sample of suspended impurities and the like. The latter may be accomplished by filtration, sedimentation, centrifigation, or any other suitable conventional technique. However, it should be appreciated that the acidity of the medium should preferably be above about a pH of about 6.0. Thus, if it is desired to analyze a highly acidic sample, such as for example, stomach contents or the like, the sample should be neutralized prior to analysis. The pH of the medium assayed preferably ranges between about 7 to about 12.

The chromogenic ionophores of the invention may be used in neutral or basic media to an extent, and demonstrate a measurable change in absorption maximum or reflectivity upon binding to ion. However, the fluorogenic reagent ionophores of the invention offer the greatest advantage for operating in neutral or basic media, and thus are preferred for use in such systems, especially when in vivo monitoring is desired.

The compounds of the invention may be used as reagent ionophores in solution for use in the detection of ions. Concentrations of reagent ionophores may vary widely according to the ionophore utilized and the medium in which ion detection is to take place. Hence, any concentration that serves to complex with an ion in a given medium may be utilized, and one skilled in the art will readily appreciate that concentrations of ionophore may be optimized. However, the present inventors have discovered that when reagent ionophores are used in a water/ethanol solution system, a preferred concentration of reagent ionophore is about $2.10^{-5}M$ to about $3.10^{-4}M$. These preferred ranges help to avoid self-quenching by the ionophores.

The maximum fluorescence efficiency for fluorogenic ionophores (such as the one described above) is expected to be about $10^{-4}M$ concentration of the ionophore (See Example 7). Above this concentration, the fluorescence emission may be expected to decrease due to self-quenching.

The compounds may also be immobilized by conventional techniques for use as a reagent ionophore, such as by dispersing the compound in a matrix, such as a polymer matrix. Other possibilities include chemical attachment of the compound to matrix components or conventional solid supports. When so immobilized, the concentration of ionophore may then vary widely and can be increased beyond $3.10^{-4}M$. Self-quenching is not a factor in this situation.

Matrices are particularly suited for use with the chromogenic ionophores of the invention. Suitable matrix components in this regard are any materials that can serve to disperse the chromogenic reagent ionophore in a substantially homogeneous manner. Homogeneity will facilitate provision of a uniform surface for contact with a sample that possibly contains a metal ion under investigation. The matrix component should be a dispersant medium that is appreciably inert, in that it is not inhibitory of desired color development. Further, it is preferred that the matrix be translucent or transparent so that optical properties, such as UV absorption, reflectance, fluoroescence, and the like may be accurately measured. Other forms of immobilization include depositing the reagent onto optic fibers and the like, by conventional techniques.

The detectability range of the reagent ionophores of the present invention for ions varies widely according to the ion it is desired to detect and the medium in which detection takes place. One skilled in the art will appreciate that the concentration of the analyte ion over which it may be detected by a given fluorogenic ionophore may be established by dissolving known amounts of the ion in a solution of the ionophore, and plotting fluorescence emission values against ion concentration. It is generally preferred that about a $10^{-4}M$ solution of the ionophore be utilized for this purpose. Plots such as these are conventionally used as standards against which emission values from a sample containing an unknown concentration of ion may be compared, to thus determine the unknown concentration of ion in the sample. Similar ranges of detection capability may be determined for the chromogenic ionophores, by measuring and plotting changes in absorption values. Visual color changes may also be standardized for certain concentrations to develop standard color charts.

Figure 6:
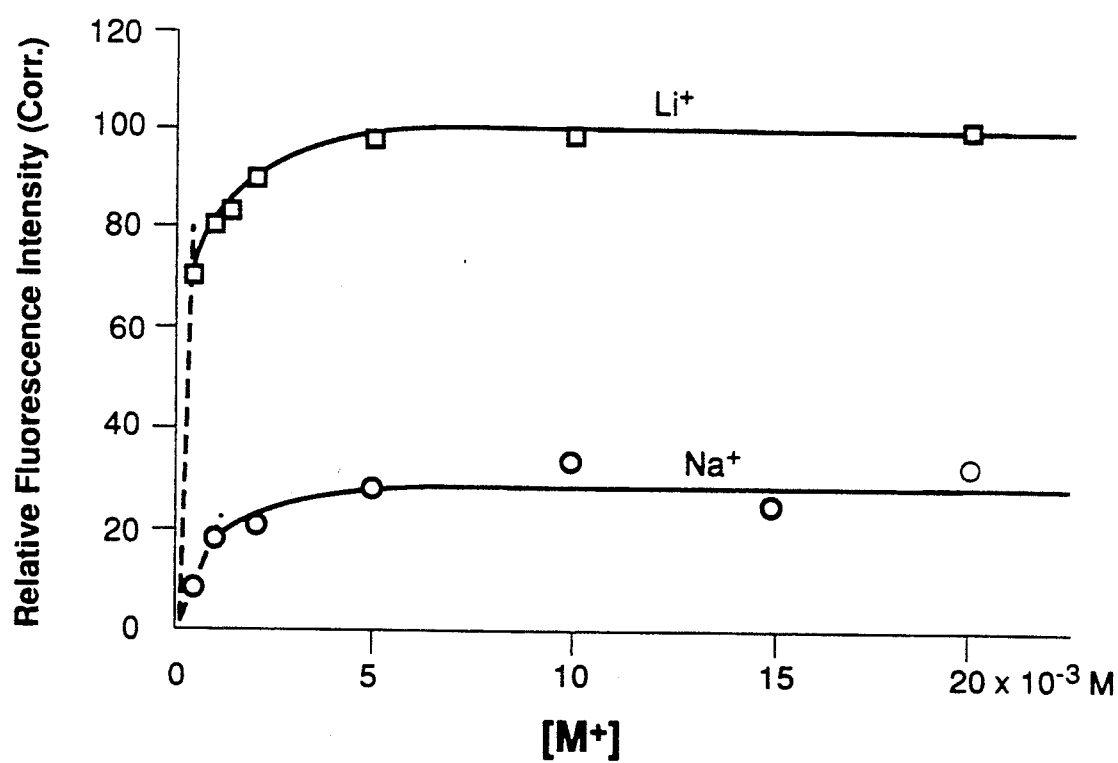
FIG. 6 depicts a graph of the relative fluorescence intensity of 6,7-(4-methyl) coumaro [211] cryptand versus changes in concentration of $Na^+$ and $Li^+$.

With respect to the detection of lithium ion, the present inventors have discovered that in the case of 6,7-(4-methyl)coumaro[211] cryptand, the fluorescence emission increases on adding lithium ion in amounts of up to about 5 mmol/L and attains a limiting value at about 6 mmol/L (FIG. 6). Thus, the detection capability of this reagent ionophore for lithium ion appears to be about 0 to about 6 mmol/L lithium ion. Sodium also shows an increase in fluorescence emission until a concentration of about 6 mmol/L. However, the maximum fluorescence enhancement is less than about 25% of that observed for lithium ion, and thus, lithium ion may be detected in the presence of sodium ion.

Interference in fluorescence caused by sodium ion in a system such as this can also be selectively suppressed by altering the medium in which detection takes place. This may be accomplished by adding a known excess of a commercially available sodium ion selective nonphotoresponsive ionophore, as for example, about 120 to about 180 mmol/L of Kryptofix ® 221. In this manner the detectability range for lithium ion can thus be modified to range from about 0–20 mmol/L lithium ion, while sodium ion does not interfere (See FIG. 7). Other examples of possible modifications would be to attach a [221] cryptand to a polymer backbone (J. Nuclear Sci. & Technol., 1983, 20, 439–440). This construct is capable of sequestering sodium ion by precipitation and is preferred in some cases over the use of Kryptofix ® 221 in improving both the selectivity and the sensitivity of the 6,7-(4-methyl)coumaro [211] cryptand for lithium ion.

With respect to detection of potassium ion, a plot of fluorescence emission of a $10^{-4}M$ solution of 6,7(4-methyl)coumaro [222] cryptand against potassium ion concentration shows a selective limiting value at about 15 mmol/L potassium ion. Therefore, it is believed that the preferred range for detecting potassium ion using this ionophore is from about 0 to about 15 mmol/L potassium ion, which is well above the anticipated level of this ion in biological samples such as human blood serum. Similar ranges for detection of sodium ion with 6,7-(4-methyl)coumaro [221] cryptand are also preferred.

In addition to selective sequestering of interfering ions as noted above, the range of detection and quantitation capabilities of the reagent ionophores of the invention can be increased by other means. For example, one of skill in the art will appreciate that a sample containing a high concentration of the ion under investigation may be diluted so that the concentration of the ion will fall within the optimum range of its detectability. As alluded to previously, a second approach may be to immobilize the ionophore to a solid surface by conventional techniques. Immobilization will prevent self-quenching and the detectability range can be extended by increasing the loading levels of the immobilized ionophore, so that there is more reagent ionophore available for complexing.

The ionophores of the present invention may be used in many diverse applications wherein it is desired to detect specific ions ionophores selective for potassium ion are of interest in the fast and accurate determination of these ions in body fluids and the like. Fluorogenic ionophores selective for potassium can be used in reagent kits, and conventional protocols may be easily developed for mixing a solution, preferably an alcoholic solution of the ionophore with blood serum samples, and then to measure potassium using fluorescence spectrophotometers. The present inventors have discovered that representative ionophores of the present invention are stable for a long period of time in aqueous and alcoholic solutions, and thus, these are the preferred solutions. Chromogenic ionophores may also be used in reagent kits. For example, they may be coated onto plastic strips or filter paper and used as dip sticks for serum analysis. Ion concentration can be determined by matching a color change with a standard color charts by visual or reflectance measurement techniques as detailed previously.

The fluorogenic ionophores can also be incorporated in fiber optic-based automatic analytical instruments, especially bifurcated fiber optics. For example, the fluorogenic ionophore may be immobilized at the terminal end of conventional optic fibers, or a solution of the ionophore may be contacted with the optic fiber using a sensor cap provided with a permeable membrane for the transport of ions into the sensor cap. One branch of the bifurcated fiber optic may thus carry the light for excitation, while the other branch may carry the fluorescence emission. Optical sensors using fiber optics have a number of advantages over electrochemical sensors. First, they do not require reference signals, and second, because the primary signal is optical, it is not subject to electrical disturbances such as those arising from surface potentials. Optical sensors can measure concentrations of the target ions without significantly disturbing the sample, and can thus be used for continuous monitoring, an example of which is the in vivo monitoring of potassium ion in the human blood during surgery. Fiber optic-based sensors also offer the advantage that the signal can be transmitted over long distances (about 2-100 meters) thus facilitating remote sensing. Further, they are amenable to miniaturization.

Certain ionophores of this invention preferentially complex with sodium ion, resulting in enhanced fluorescence or color change. These can be used to develop test kits or fiber optic-based sensors for detecting sodium ion. One example of this is in the detection of leakage of sea water into electronic instruments in towed arrays for sonar sensing or in reusable booster rockets used in launching vehicles into outer space.

Chemical analogues of certain of the preferred fluorogenic reagents may also be used for developing ion-selective Field Effect Transistors (FETs). In one such embodiment, FETs are electronic switching devices which can be used in turning on an alarm when sea water leaks occur. The ionophore is covalently bound to the surface oxygens of an inorganic insulator such as silica, alumina, thoria and the like. Since the fluorogenic ionophores of the invention are especially efficient in transmitting electronic perturbations, one may expect that modulation of the electric potentials "seen" by the FETs will occur when targeted ions are bound to the ionophores. An example of this is a sea water leakage warning system. When contacted with sea water, the sodium ion complexes with the ionophore-based FET, thus affecting the output voltage of the FET amplifier. Such voltage changes can set off an alarm.

Ionophores selective for lithium ion are useful in the detection of therapeutic levels of lithium in blood serum. Lithium has an important role in the management of a number of psychiatric disorders. Lithium is administered orally in the form of tablets, capsules, or liquid. Because lithium has the potential for having adverse effects on the kidneys and thyroid, it is important to carefully control the lithium dosage. Heretofore, the blood (serum) lithium level has been monitored through time-consuming and expensive procedures of flame photometry or atomic absorption spectrophotometry (See Toxicology and Therapeutic Drug Monitoring, Chap. 61, "Lithium" pp. 1377-1379).

In one embodiment of the present invention, there is provided a fluorogenic reagent and analytical system for the monitoring of lithium content of blood. This indicator system will aid the clinician in the rapid and inexpensive control of lithium dosage, to provide a dosage regime that is likely to be therapeutic without running the risk of toxicity. The present reagent is particularly suited for this analysis of blood serum, for the detection of lithium used for medical treatment even in the presence of substantial amounts of naturally occurring sodium and potassium ions. Lithium has a relatively narrow therapeutic range. Doses of 0.7-1.7 mmol/L can alleviate acute manic symptoms in some cases, while doses of about 2.0 mmol/L or above can be toxic. The sensitivity of the present fluorogenic indicator is within this critical range. In general, concentrations as low as 0.1 mmol/L may be detected.

In another preferred embodiment, chromophoric ionophores are coated onto a suitable substrate to prepare a test strip or disk or the like. The resulting solid indicator may then be dipped into a liquid sample under analysis, or a drop of sample placed onto it. Various concentrations of sample under analysis may be tested and the development of color hue may be visually compared against that produced by a known concentration of lithium. Alternatively, the presence of lithium may be detected by a change in reflectivity utilizing conventional analytical devices for this purpose, such as those described for a reflectance spectrum.

The following are more specific embodiments of the present invention, and are not to be considered limitative thereof.

GENERAL PROCEDURE FOR THE PREPARATION OF PREFERRED CRYPTANDS, REAGENT IONOPHORES AND SELECTIVE BINDING OF IONS TO THE IONOPHORES

Commercially available 4-methylesculetin (6,7-dihydroxy-4-methylcoumarin) was first converted to 6,7-di(2'-hydroxyethyl)-4-methylcoumarin by reaction with 2-bromoethanol. (See Example 1). The reaction of this compound with thionyl chloride in toluene in the presence of pyridine (See Example 2) produced 6,7-di(2'-chloroethyl)-4-methylcoumarin which was then converted to the corresponding diiodo compound by reacting it with sodium iodide in refluxing acetone (See Example 3). The diiodo compound was reacted with one mole equivalent of commercially available 1,10-diaza-18-crown-6 in acetonitrile under reflux in the presence of sodium carbonate. The compound (6.7-(4-methyl)-coumaro [222] cryptand) was prepared and purified as its sodium complex over an alumina column and confirmed by infrared, $^1$HNMR spectroscopy and fast atom bombardment (FAB) mass spectrometry (see Example 4). The sodium ion could be easily replaced by potassium ion on contact with an aqueous solutions of potassium chloride. The structure of 6,7-(4-methyl)coumaro [222] cryptand is shown below:

Structure 17

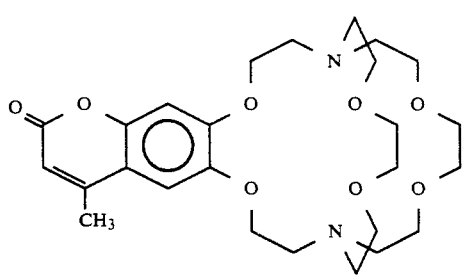

The 6,7-(4-methyl) coumaro [221] cryptand was prepared from the diiodo compound and 1,7-diaza-15-crown-5 in refluxing acetonitrile in the presence of lithium carbonate. After purification, the compound was obtained as the sodium iodide complex, although no sodium containing reagents were employed in the preparation (see Example 5). Presumably, sodium ions were extracted by this ionophore out of glassware and/or alumina used in chromatographic purification. The strong affinity of this compound for sodium ion is thus demonstrated. On shaking 0.75 g of the sodium iodide complexed ionophores with 20 mL of a 10% ethanolic solution of calcium chloride in a polyethylene bottle, the sodium ion was more than 80% exchanged for calcium ion. This compound is as shown below:

Structure 18

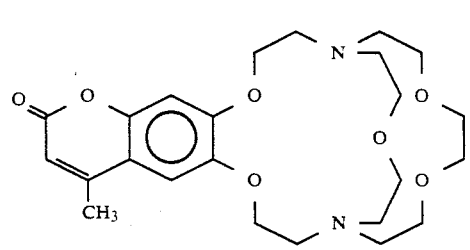

The 6,7-(4-methyl) coumaro [211] cryptand was prepared from the diiodo compound and 1,7-diaza-12-crown-4 (synthesized according to the procedure of J. M. Lehn, U.S. Pat. No. 3,888,877. Jun. 10, 1975) in the presence of 1,8-bis(dimethylamino) naphthalene. The ion-free ionophore was purified over alumina (See Example 6) and confirmed by infrared, $^1$HNMR and mass spectrometry. It may be depicted as follows:

Structure 19

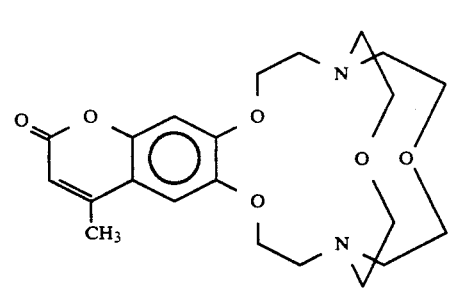

Fluorescence Spectra of Preferred Reagents

Figure 8:
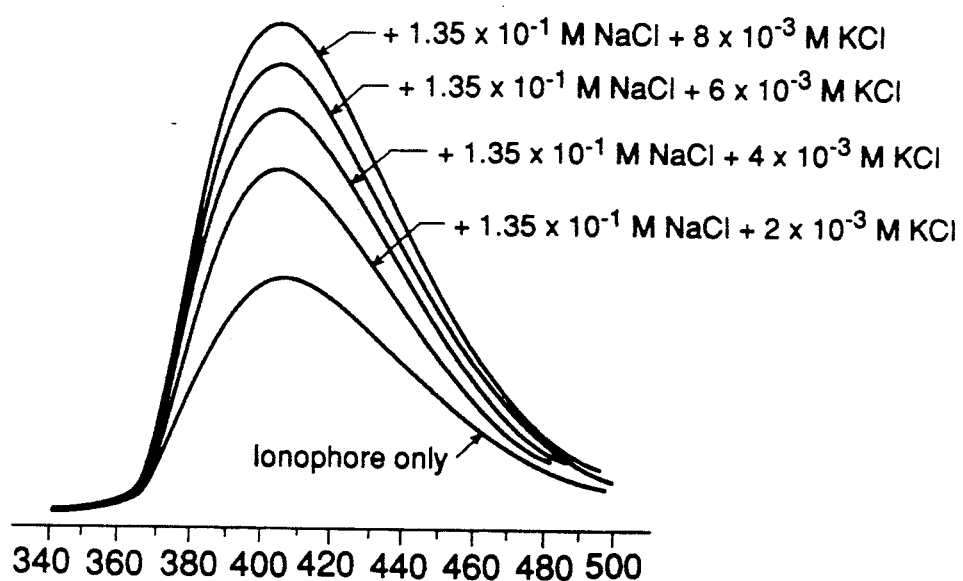
FIG. 8 depicts a graph of fluorescence of 6,7-(4-methyl) coumaro [222] cryptand relative to binding of potassium ion in the presence of serum-like concentrations of sodium ion.

The fluorescence excitation spectra of the compounds show close similarity to their absorption spectra. Fluorescence measurements were carried out in a neutral 50/50 ethanol/water medium using exciting wavelength of 330 nm and scanning emission wavelengths between 340–540 nm, giving a broad peak with a maximum at 410 nm. Addition of metal ions to the solution did not change the UV spectrum. However, selective enhancement of fluorescence was observed when the metal ion with the best "fit" in the ionophore cavity was added. Thus, 6,7-(4-methyl) coumaro [222] cryptand (Structure 17), with its ionophore cavity ideally suited for accommodating potassium ion, showed a dramatic enhancement of fluorescence for this ion. Sodium and lithium ions showed very little change in fluorescence intensity. (See FIG. 2). In human blood serum, the level of sodium is high (135–148 mmol/L) while that for potassium ion ranges from 3.5–5.3 mmol/L. FIG. 8 shows that 6,7-(4-methyl) coumaro [222] cryptand can quantitatively measure changes in the concentration of the potassium ion ranging from 2 to 8 mmol/L in the presence of 135 mmol/L of sodium ion at neutral pH. The ionophore could therefore be ideally suited for a fluorescence-based sensor for the direct monitoring of potassium ion in blood serum and other biological fluids. It should be noted that there is no kinetic barrier to complex formation between the ionophores and metal ions. The equilibrium is established rapidly, and thus, continuous monitoring is made possible.

Figure 3:
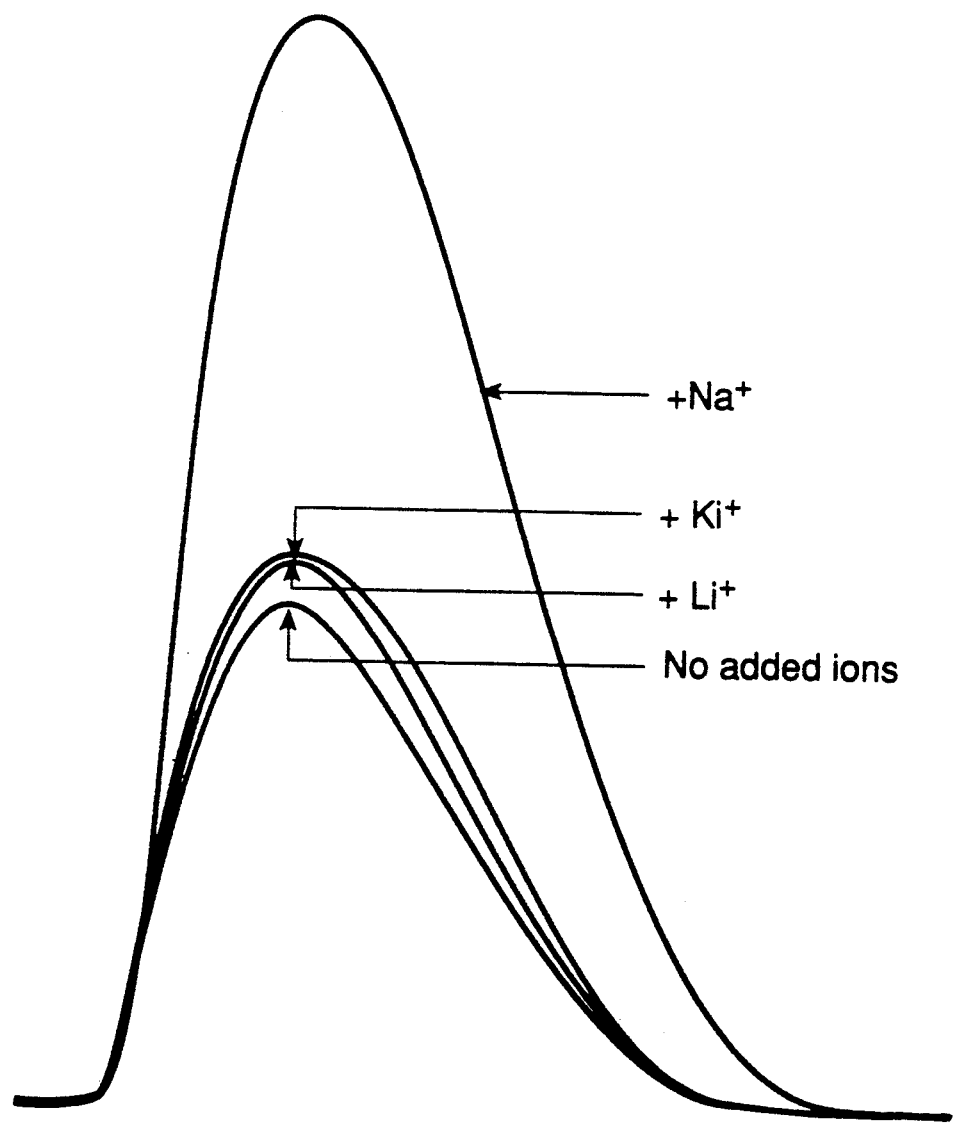
FIG. 3 depicts selective enhancement of fluorescence of 6,7-(4-methyl) coumaro [221] cryptand upon binding with sodium ion.

The ionophore cavity in 6,7-(4-methyl) coumaro [221] cryptand (Structure 18) is ideal for accommodating sodium ion. A dramatic enhancement of its fluorescence was observed when the calcium ion-bound 6,7-(4-methyl) coumaro [221] cryptand dissolved in 50/50 ethanol/water was treated with sodium ion, potassium and lithium ions showed very little effect on its fluorescence. (FIG. 3). This ionophore is suited for the quantitative determination of sodium ion, even in the presence of a large excess of potassium, lithium, and calcium ions.

Figure 4:
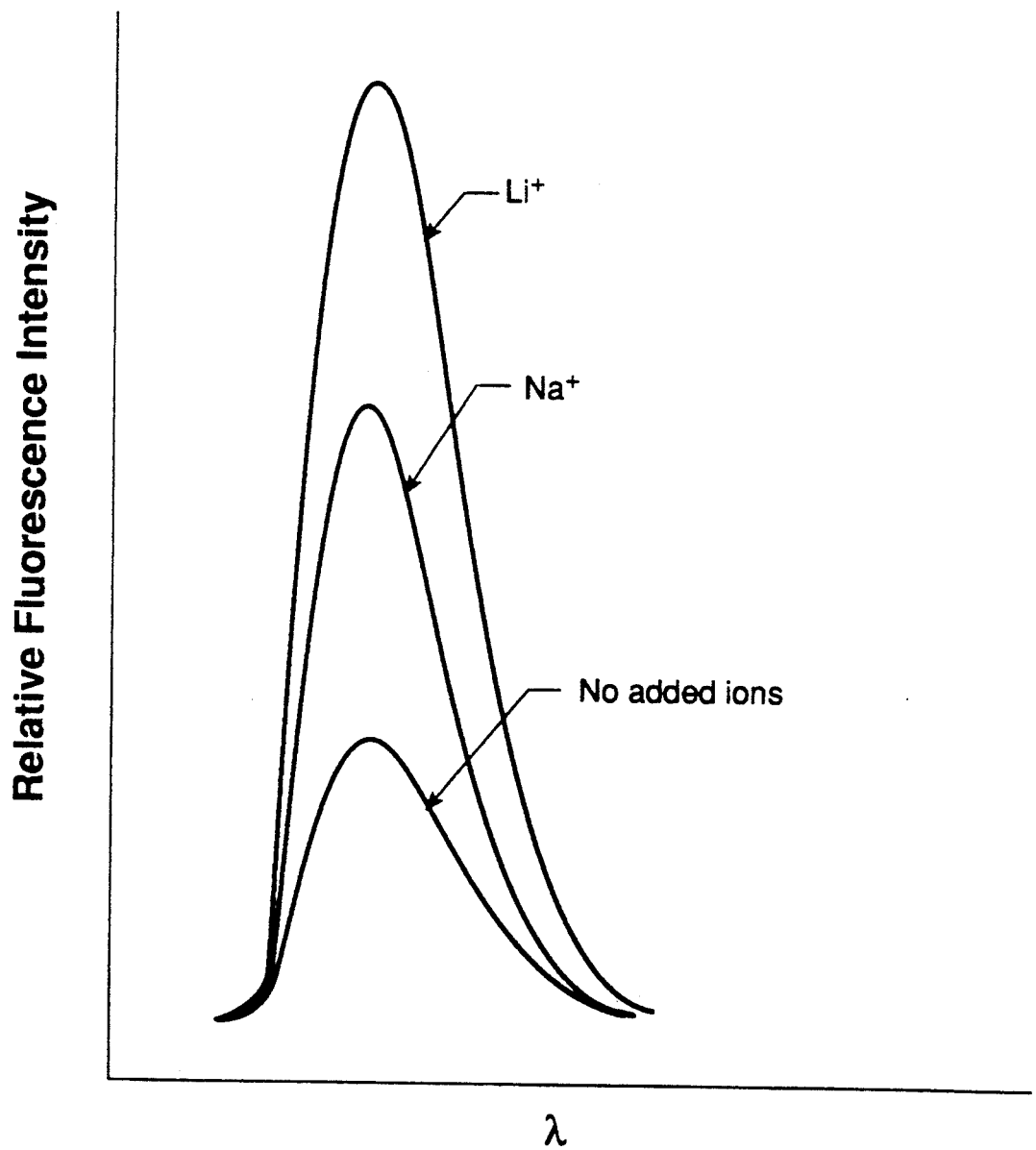
FIG. 4 depicts selective enhancement of fluorescence of 6.7-(4-methyl) coumaro [211] cryptand upon binding with lithium ion.
Figure 5:
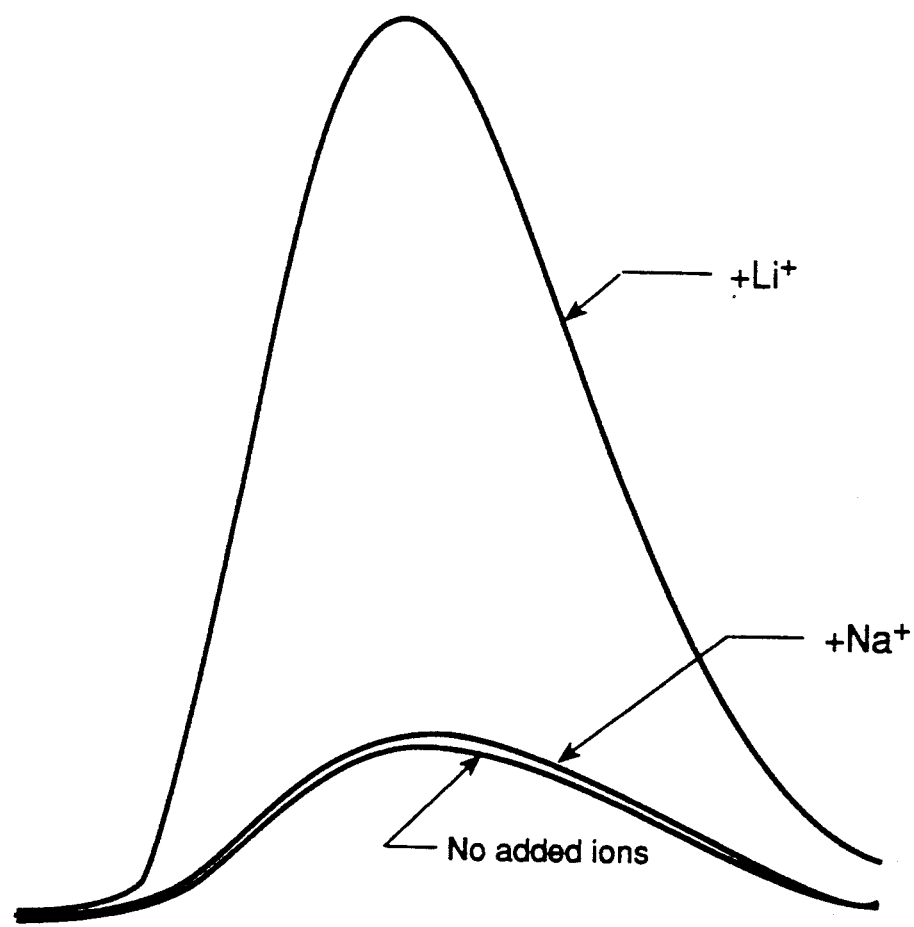
FIG. 5 depicts selective enhancement of fluorescence of 6,7-(4-methyl) coumaro [211] cryptand upon binding with lithium ion in the presence of Kryptofix ® 221.

The 6,7-(4-methyl) coumaro [211] cryptand (Structure 19) shows a dramatic enhancement of fluorescence With lithium ion. The ionophore cavity is somewhat large (1.6Å diameter) compared to the size of the lithium ion (1.2Å diameter). Thus, sodium ion (1.9Å diameter) also shows considerable enhancement of fluorescence. (FIG. 4). The selectivity of this reagent for lithium ion in competition with sodium ion can be improved by using commercially available Kryptofix® 221 which is a non-photoresponsive ionophore. (FIG. 5). Using a known excess of Kryptofix® 221 along with 6,7-(4-methyl) coumaro [211] cryptand, it was possible to quantitatively measure 0.5 to 6.0 mmol/L of lithium ion in the presence of 140 mmol/L of sodium ion. (See FIG. 9). Human blood serum normally contains less than 0.3 mmol/L and the toxic range is from 3 to 6 mmol/L. The ability of 6,7-(4-methyl) coumaro [211] cryptand to measure lithium ion at therapeutic levels in blood serum in the presence of 140 mmol/L sodium ion, is demonstrated by the data presented in FIG. 9.

The following is a more specific account of the synthesis of certain of the reagent ionophores and experiments testing their ion selectivity.

EXAMPLE 1

Preparation of 6,7-Di-(2'-hydroxyethoxy)-4-methylcoumarin

A solution of 9.6 g of 6,7-dihydroxy-4-methyl coumarin and 12,5 g of 2-bromoethanol in 375 ml of anhydrous acetonitrile and 75 ml of anhydrous N,N-dimethylformamide are stirred with 21.0 g of anhydrous potassium fluoride under a nitrogen atmosphere and heated at 75° for 7 days. After cooling slightly, the solution is filtered and the filtrate is evaporated to dryness. A brown solid, title compound, remains. Yield 90%: $^1$HNMR (DMSO - $d_6$) δ 7.2 (s, 1H). 7.05 (s, 1H), 6.2 (s, 1H), 4.1(m, 4H), 3.75 (m, 4H), 2.4 (s, 3H).

EXAMPLE 2

Preparation of 6,7-Di-(2'-chloroethoxy)-4-methylcoumarin

A solution of 17 g of the dihydroxy compound obtained in Example 1 and 12 g of pyridine in 800 ml of anhydrous toluene are stirred and heated to 40° under a nitrogen atmosphere. 18.1 g of thionyl chloride are added over a period of 25 minutes under agitation. The mixture is heated at reflux temperature for 3 hours. After cooling to ambient temperature, the solution is decanted. The residue is broken up, washed with water and toluene and combined with the supernatent liquid. The organic layer is separated and washed with dilute hydrochloric acid, then saturated sodium bicarbonate solution. The organic layer is separated, dried ($Na_2SO_4$) and evaporated. Yield 61%: $^1$HNMR (CDCl$_3$) δ 7.15 (s, 1H), 6.8 (s, 1H), 6.15 (s, 1H), 4.35 (m, 4H), 3.9 (m, 4H), 2.4 (s, 3H).

EXAMPLE 3

Preparation of 6,7-Di-(2'-iodoethoxy)-4-methylcoumarin

A solution of 11.6 g of the dichloride obtained in Example 2 and 13.7 g of anhydrous sodium iodide in 130 ml of anhydrous acetone are stirred under a nitrogen atmosphere and heated at reflux temperature for 4 days. After cooling to ambient temperature, the solution is evaporated to dryness. The solid residue is dissolved in dichloromethane and washed with a sodium thiosulfate solution. The organic layer is separated, dried ($Na_2SO_4$), and evaporated to dryness giving the crude product. Purification on deactivated alumina with mobile phase of dichloromethane with 10% ether gives the title compound Yield 49%: IR 1741 cm$^{-1}$ (α, β-unsaturated δ-lactone C=O); $^1$HNMR (CDCl$_3$) δ 7.1 (s, 1H), 6.75 (s, 1H), 6.15 (s, 1H), 4.4 (m, 4H), 3.5 (m, 4H), 2.4 (s, 3H); FABMS 501 (M+H).

EXAMPLE 4

Preparation of 6,7-(4-methyl) coumaro 222] cryptand

A solution of 0.55 g of the purified diiodide obtained in Example 3 and 0.29 g of 1,10-diaza-18-crown-6 ln 45 ml of anhydrous acetonitrile are stirred with 0.47 g of sodium carbonate under a nitrogen atmosphere and heated at reflux temperature for 6 days. After cooling to ambient temperature, the solution is evaporated to dryness. The solid residue is dissolved in chloroform and washed with saturated sodium chloride solution. The organic layer is separated, dried ($Na_2SO_4$) and evaporated to dryness to give the crude product. Purification on alumina with mobile phase of 1/1 tetrahydrofuran/dichloromethane followed by 85/10/5 dichloromethane/ether/methanol gives the purified title compound with bound sodium ion as indicated by FABMS. Yield 60%: IR 1708 cm$^{-1}$ (α, β-unsaturated δ-lactone C=O): $^1$HNMR (CDCl$_3$) w 7.25 (s, 1H), 6.85 (s, 1H), 6.15 (s, 1H), 4.40 (t, 2H), 4.30 (t, 2H), 3.55 (m, 16H), 2.98 (t, 2H), 2.91 (t, 2H), 2.75 (m, 8H), 2.50 (s, 3H); FABMS 507 (M+H), 529 (M+Na), 545 (M+K); UV (50% $CH_3CH_2OH$) λ max (ε) 228 (5.450), 287 (1.690), 338 (3,170); fluorescence (50% $CH_3CH_2OH$) λex 330 nm, λem 340–540 nm (Peak at 410 nm).

EXAMPLE 5

Preparation of 6,7-(4-methyl) coumaro [221] cryptand

A solution of 0.95 g of the purified diiodide obtained in Example 3 and 0.41 g of 1.7-diaza-15-crown-5 in 90 ml of anhydrous acetonitrile are stirred with 1.12 g of lithium carbonate and 4 drops of water to activate the base, under a nitrogen atmosphere and heated at reflux temperature for 6 days. After cooling to ambient temperature, the solution is filtered and the filtrate is evaporated to dryness to give the crude product.

Purification continues as Example 4, giving the title compound with bound sodium ion as indicated by FABMS. Since sodium was not added during any step of the preparation, it is assumed that sodium ion contamination is caused by glassware. In an experiment to exchange bound sodium ion for calcium ion, 0.75 g of the sodium-bound ionophore in 20 ml of absolute ethanol and 2 g (excess) of calcium chloride are stirred in a plastic container under a nitrogen atmosphere at ambient temperature overnight. Solvent is evaporated to half volume. Excess calcium chloride precipitate is removed by filtering. Filtrate is again evaporated to half volume and excess salt is removed. The remaining filtrate is evaporated to dryness. FABMS confirms that exchange is greater than 80% complete: m/z 537 (M+Ca$^{+2}$+Cl$^-$) with Cl$^-$ isotope pattern. Yield 50%: IR 1705 cm$^{-1}$ (α, β-unsaturated δ-lactone C=O); $^1$HNMR (CDCl$_3$)δ 7.35 (s, 1H) 7.0 (s, 1H), 6.2 (s, 1H), 4.4 (m, 4H), 3.8 (m, 12H), 3.0 (m, 12H), 2.5 (s, 3H); FABMS 463 (M+H), 469 (M+Li), 485 (M+Na); UV (50% $CH_3CH_2OH$) λmax (ε) 227 (15,000), 288 (3.920), 339 (8.600); fluorescence (50% $CH_3CH_2OH$) λ ex 330 nm, λem 340–540 nm (Peak at 410 nm).

EXAMPLE 6

Preparation of 6.7(4-methyl) coumaro [211] cryptand

A solution of 0.5 g of the purified diiodide obtained in Example 3 and 0.174 g of 1.7-diaza-12-crown-4 (Ref. J. M. Lehn, U.S. Pat. No. 3,888,877 Jun. 10, 1975) in 50 ml of anhydrous acetonitrile are stirred with 0.45 g of 1,8-bis(dimethylamino) naphthalene under a nitrogen atmosphere and heated at reflux temperature for 6 days. After cooling to ambient temperature the solution is evaporated to dryness. The solid residue is dissolved in chloroform and filtered. The filtrate is evaporated to dryness to give the crude product. Purification continues as in Example 4, giving the title compound free of any bound metal ion as indicated by MSFAB. Yield 30%: IR 1708 cm$^{-1}$ (α, β-unsaturated w -lactone C=0); $^1$HNMR (CDCl$_3$) δ7.1 (s, 1H), 6.85 (s, 1H), 6.15 (s, 1H), 4.3 (m, 4H), 3.5 (m, 8H), 2.9 (m, 12H), 2.5 (s, 3H); FABMS 419 (M+H). 441 (M+Na); UV (50% $CH_3CH_2OH$) g max ( e ) 226 (16,350), 287 (4,460), 336 (8,820); fluorescence (50% $CH_3CH_2OH$) λex 330 nm, λem 340–540 nm (Peak at 410 nm).

EXAMPLE 7

Determining the Ionophore Concentration For Maximum Fluorescence Efficiency

A stock solution of the ionophore at the concentration of $10^{-3}M$ in 50/50 ethanol/water at neutral pH was prepared. Fluorescence measurements were taken at ambient temperature using exciting wavelength of 330 nm and scanning emission wavelengths from 340–540 nm giving a broad peak With maximum at 410 nm. Measurements were made on solutions ranging in concentration from $10^{-5}M$ to $10^{-3}M$. Over this range, UV absorption obeys Beer's law whereas fluorescence emission increases from $10^{-5}M$ to $10^{-4}M$, but then decreases from $10^{-4}M$ to $10^{-3}M$. This study indicates that under these conditions, the optimum concentration is about $10^{-4}M$ for maximum fluorescence efficiency. (see FIG. 1).

EXAMPLE 8

Selectivity of 6,7-(4-methyl) coumaro [222] cryptand for potassium ion.

Figure 2:
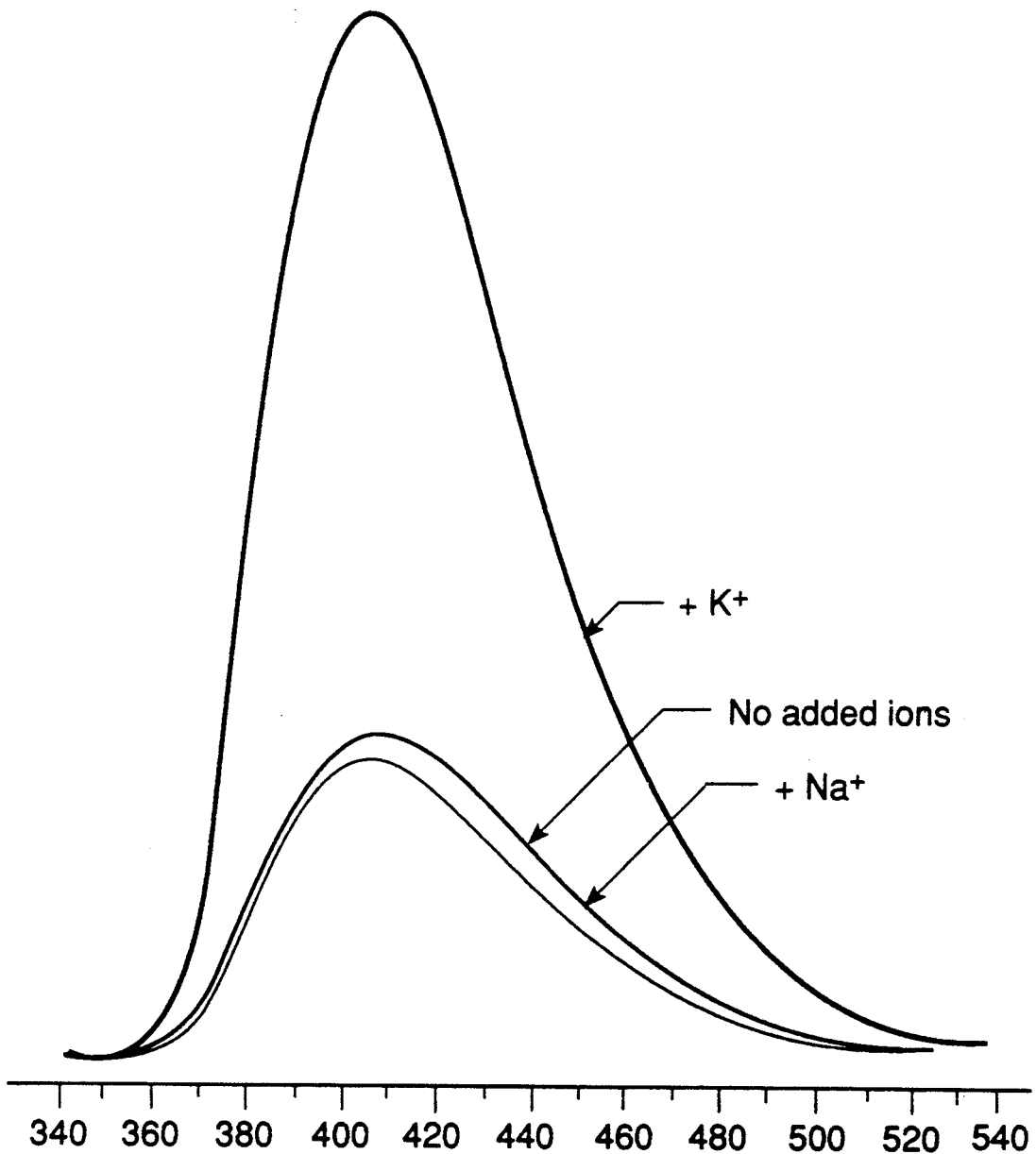
FIG. 2 depicts selective enhancement of fluorescence of 6,7-(4-methyl) coumaro [222] cryptand upon binding with potassium ion.

The sodium iodide-complexed 6,7-(4-methyl) coumaro[222] cryptand was taken at $10^{-4}M$ in 50/50 ethanol/water at neutral pH. Fluorescence measurements were made at ambient temperature using exciting wavelength of 330 nm and scanning emission wavelengths from 340–540 nm giving a broad peak with maximum at 410 nm. The addition of one drop of 1M potassium chloride solution to 2.5 ml of the ionophore solution in a cuvette resulted in a dramatic enhancement of fluorescence emission. On the other hand, addition of one drop of 1M sodium chloride resulted in a slight quenching of the fluorescence. Addition of lithium chloride showed very little change in fluorescence (FIG. 2). This experiment demonstrates that the ionophore is a selective indicator for potassium ion.

EXAMPLE 9

Selectivity of 6,7-(4-methyl) coumaro[221] cryptand for sodium ion.

The experiment described in Example 8 was repeated with a $10^{-4}M$ calcium chloride-complexed 6,7-(4-methyl) coumaro[221] cryptand. The addition of one drop of 1M sodium chloride showed a dramatic enhancement of fluorescence emission while potassium chloride and lithium chloride showed very little change (FIG. 3) thus establishing the selectivity of this ionophore for sodium ion.

EXAMPLE 10

Selectivity of 6,7-(4-methyl) coumaro[211] cryptand for lithium ion.

The experiment described in Example 8 was repeated for 6,7-(4-methyl) coumaro[211] cryptand which showed an enhancement of fluorescence emission for lithium chloride. However, sodium chloride also shows considerable enhancement of fluorescence whereas potassium chloride shows no effect at all (FIG. 4). In order to improve the selectivity of this cryptand for lithium ion over sodium ion, a large excess (140 mmol/L) of a commercially available cryptand, Kryptofix ® 221 (Structure 15) a non-photoresponsive ionophore known to be selective for sodium ion, was added to the stock solution. The addition of lithium chloride to this solution enhances the fluorescence emission while the addition of sodium chloride has little effect (FIG. 5).

EXAMPLE 11

Evaluation of ion detection limits of fluoroqenic ionophores.

Figure 7:
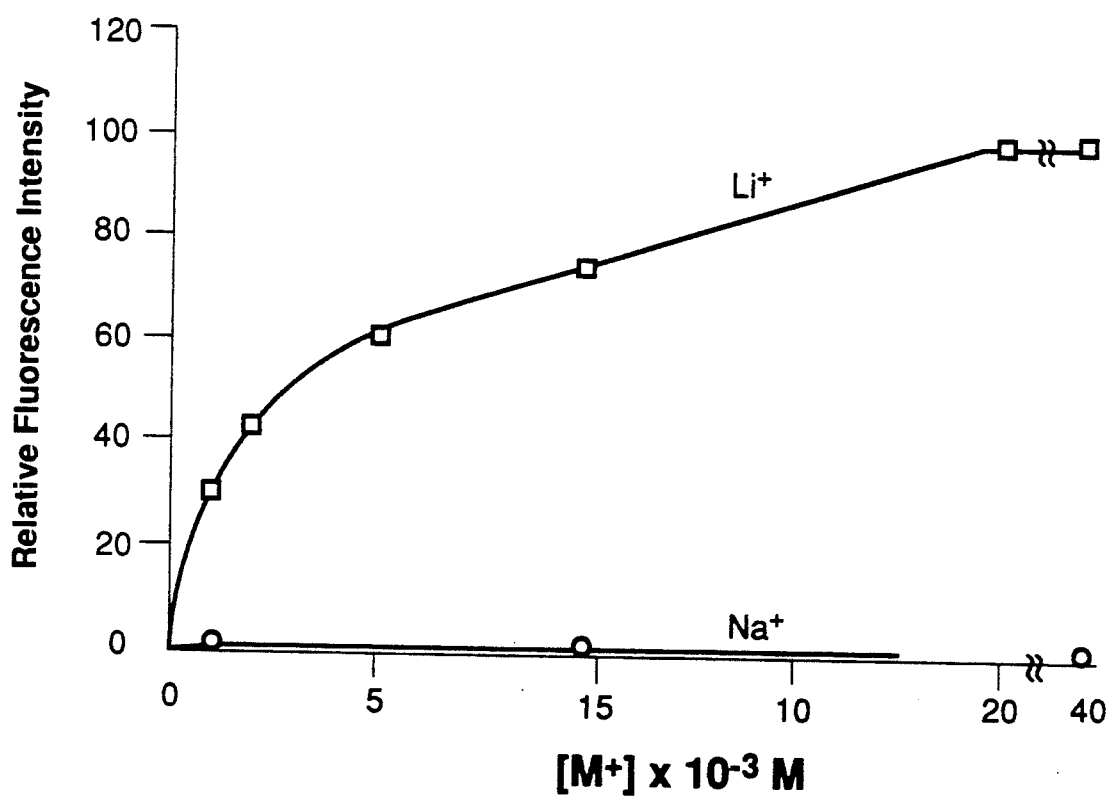
FIG. 7 depicts a graph of the changes in relative fluorescence intensity of 6,7-(4-methyl) coumaro [211] cryptand versus changes in concentration of Na+ and Li+ in the presence of Kryptofix® 221.

Solutions of fluorogenic ionophores ($10^{-4}M$) in 50/50 ethanol/Water containing varying amounts of a given salt (lithium chloride, sodium chloride or potassium chloride) were prepared. The fluorescence emissions of these solutions were measured (as described in Example 8) and plotted against salt concentrations. FIG. 6 shows such a plot for 6,7-(4-methyl) coumaro[211] cryptand against lithium chloride and sodium chloride. A limiting value of fluorescence enhancement was observed for lithium chloride and sodium chloride above 6 mmol/L. However, the fluorescence enhancement for sodium chloride is poor (less than 25% the value observed for lithium chloride) and thus the ionophore is not preferred for quantitative measurement of sodium ion. The selectivity of the ionophore for lithium ion over sodium ion can be dramatically improved by adding known excess ($1.5 \times 10^{-1}$ mmol/L) of Kryptofix ® 221 to the stock solution. FIG. 7 shows that the limiting value for lithium chloride in this solution to be 20 mmol/L while sodium chloride does not significantly affect the fluorescence. The system is now highly selective for lithium ion.

A plot similar to that depicted in FIG. 6, with limiting value of 15 mmol/L for potassium chloride, was obtained for 6,7-(4-methyl) coumaro[222] cryptand. Sodium and lithium ions showed very little change in fluorescence. Similar results were obtained for the 6,7-(4-methyl) coumaro[221] cryptand where a limiting value of 15 mmol/L was observed for sodium chloride while lithium chloride and postassium chloride showed very little effect on the fluorescence.

EXAMPLE 12

Quantitative analysis of potassium ion in serum-like solutions using 6,7-(4-methyl) coumaro[222] cryptand.

The selectivity and the sensitivity of 6,7-(4-methyl) coumaro[222] cryptand in the direct quantitative analysis of potassium ion in human blood serum is demonstrated in this example. The concentration of potassium ion in human blood serum varies from 3.5–5.3 mmol/L while sodium ion is present in a large excess (135–148 mmol/L). Solutions in 50/50 ethanol/water at neutral pH containing $10^{-4}M$ 6,7-(4-methyl) coumaro[222] cryptand, 135 mmol/L of sodium chloride but with varying amounts (0–8.0 mmol/L) of potassium chloride were prepared. The fluorescence emission of these solutions were measured as described in Example 8. FIG. 8 shows that the fluorescence emission of the ionophore increases with increasing amounts of potassium ion thus demonstrating the ability of the ionophore to measure small changes in potassium ion in the presence of large excess of sodium ion. (Changing the concentration of the sodium ion in the stock solution to 140 mmol/L or 150 mmol/L did not affect the fluorescence emission intensities of the ionophore significantly). Since the fluorescence intensities are reproducible and are sensitive only to changes in potassium ion concentrations, they can be used reliably in preparing standard charts (intensity vs. concentration) for potassium ion. These charts may then be used for determining the level of potassium in human serum samples.

EXAMPLE 13

Quantitative analysis of lithium ion in serum-like solution using 6,7-(4-methyl) coumaro[211] cryptand.

Figure 9:
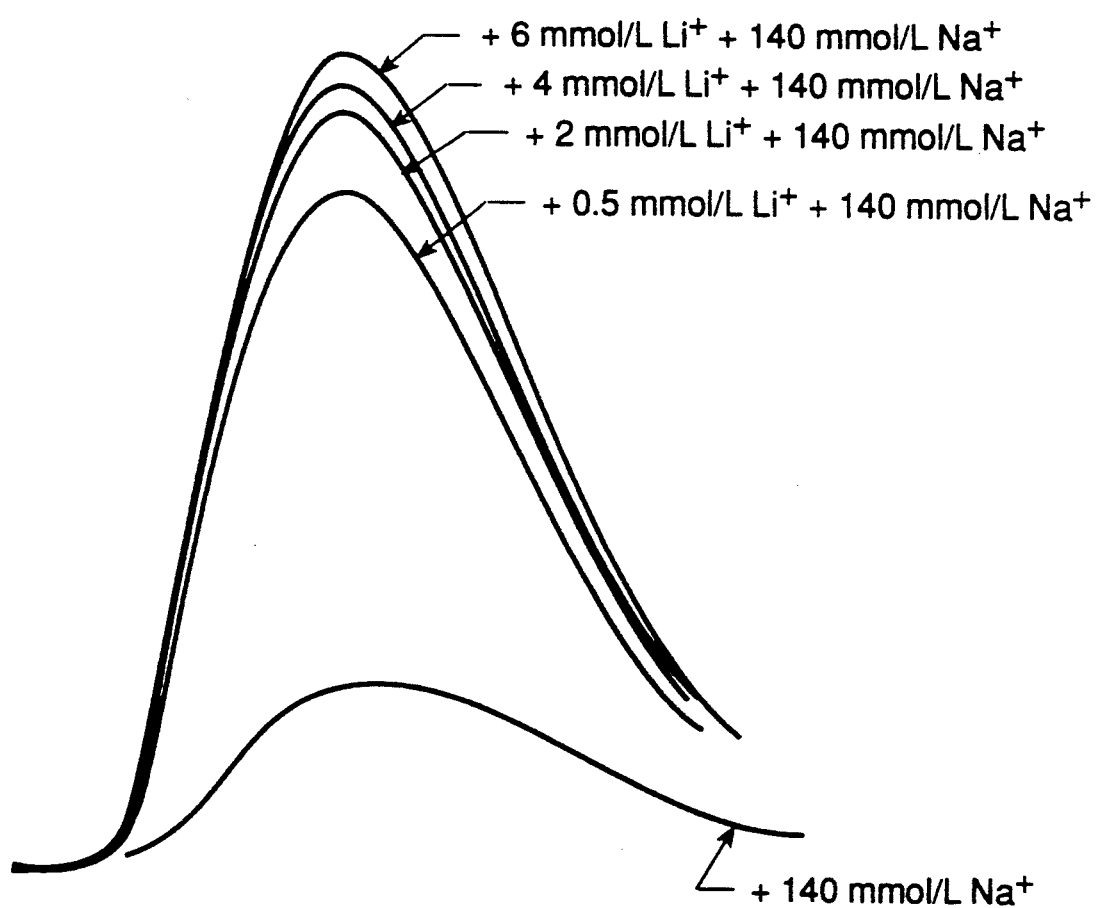
FIG. 9 depicts a graph of fluorescence of 6,7-(4-methyl coumaro [211] cryptand relative to binding of lithium ion in the presence of serum-like concentrations of sodium ion.

The ability of 6,7-(4-methyl) coumaro[211] cryptand to quantitatively analyze for lithium ion in the presence of large excess of sodium ion is demonstrated in this example. Human blood serum normally does not contain lithium ion. However, in patients undergoing lithium therapy, the preferred level of lithium in blood serum varies from 0.7–1.3 mmol/L Whereas the toxic level ranges from 3–6 mmol/L. Solutions in 50/50 ethanol/water at neutral pH containing $10^{-4}$M ionophore, 150 mmol/L of Kryptofix® 221, 140 mmol/L of sodium chloride, but with varying amounts (0–6 mmol/L) of lithium chloride were prepared. The fluorescence emission of these solutions were measured as described in Example 8. FIG. 9 shows that the fluorescence emission increases with increasing amounts of lithium ion thus demonstrating the ability of the ionophore to measure small changes in lithium ion in the presence of large excess of sodium ion. As in Example 12, fluctuations in sodium ion concentration do not affect the fluorescence intensities significantly. Under the conditions described in this example, the fluorescence intensities are sensitive only to changes in the concentration of the lithium ion and thus can be used to prepare standard charts (fluorescence intensity vs. concentration) for lithium ion. The charts may be used for determining lithium ion in blood serum. It is clear from FIG. 9 that the system is particularly sensitive to detect lithium ion in the therapeutic and toxic ranges.

EXAMPLE 14

Compatibility of the fluoroqenic and chromogenic ionophores in aqueous medium.

The experiments described in Examples 12 and 13 were repeated using water as the medium. Quantitative analysis of potassium and lithium ions were achieved. The fluorescence intensities were generally higher.

EXAMPLE 15

Preparation of 1,2-Bis-(2-chloroethoxy)-4-nitrobenzene 2.8 g of thionyl chloride are added dropwise to a stirring solution of 2.4 g of 1,2-Bis-(2-hydroxyethoxy)-4-nitrobenzene (prepared following method V of Abakumova, Kolenko and Kodess translated from Zhurnal Organicheskoi Khimii, Vol. 18No. 7, pp. 1495–1498, July 1982), and 0.9 g of pyridine in 55 ml of anhydrous toluene under a nitrogen atmosphere at 70°. After addition, the solution is heated at 110° for 18 hours. After cooling to ambient temperature, the solution is washed with 2% hydrochloric acid. The organic layer is dried ($Na_2SO_4$) and evaporated to dryness. The title compound was obtained in 80% yield.

EXAMPLE 16

Preparation of 1,2-Bis-(2-iodoethoxy)-4-nitrobenzene

A solution of 2.8 g of the dichloride obtained in Example 15 and 3.8 g of anhydrous sodium iodide in 35 ml of anhydrous acetone are stirred under a nitrogen atmosphere and heated at reflux temperature for 2 days. After cooling to ambient temperature, the solution is evaporated to dryness. The solid residue is dissolved in ether and washed with a sodium thiosulfate solution to remove iodine. The organic layer is separated, dried ($Na_2SO_4$) and evaporated to dryness, and after recrystallization from hexane the title compound is produced. Yield 60%: IR 1503 $cm^{-1}$ and 1349 (aromatic C-$NO_2$); $^1$HNMR (CDCl$_3$) δ7.83 (d, 1H), 7.77 (s, 1H), 7.0 (α, 1H), 4.38 (t, 4H), 3.48 (t, 4H); MS (CI, methane), m/z 464 (M+H), 492 (M+29), 504 (M+41), 336 (MH - HI).

EXAMPLE 17

Preparation of 7-Nitro-4,11,17,20,25,28-hexaoxa-1, 14-diazatricyclo [12,8,8,0,5,10]-triaconta-5,7,9-triene.

A solution of 2.0 g of the diiodide obtained in Example 16 and 1.0 g of 1,10-diaza-18-crown-6 in 160 ml of anhydrous acetonitrile are stirred with 1.7 g of sodium carbonate under a nitrogen atmosphere and heated at reflux temperature for 6 days. After cooling to ambient temperature, the solution is filtered and the filtrate is evaporated to dryness. The residue is dissolved in dichloromethane and passed through a column of alumina. The product is eluted with a mixture of chloroform/methanol (97/3). The solution is evaporated to dryness, leaving golden yellow flakes. Yield 79% IR 1516 $cm^{-1}$ and 1343 (aromatic C-$NO_2$); $^1$HNMR (DMSO-d$_6$) δ 7.65–8.2 (br m, 2H), 7.1–7.4 (br m, 1H), 4.1–4.25 (br m, 4H), 3.65 (s, 8H), 3.4–3.6 (br m, 8H), 2.6–3.0 (br m, 12H); FABMS 470 (M+H), 492 (M+Na), 508 (M+K).

EXAMPLE 18

Preparation of 7-Amino-4,11,17,20,25,58-hexaoxa-1,14-diazatricyclo [12,8.8,0,5,10]-triaconta-5,7,9-triene Hydrogenation of 1 g of the product obtained in Example 17 is carried out in 40 ml of ethanol with 10% palladium on carbon under 75 psig of hydrogen and heated to 75° for 18 hours. After filtering off the catalyst, the filtrate was concentrated to obtain the title compound as a brownish viscous liquid. Yield 88%: IR 3350 $cm^{-1}$ (-$NH_2$); $^1$HNMR (CDCl$_3$)δ 6.73 (d, 1H), 6.63 (d, 1H), 6.28 (m, 1H), 4.07–4.2 (m, 4H), 3.6–3.7 (m, 8H), 3.4–3.6 (m, 8H), 2.75–2.83 (m, 4H), 2.68 (m, 8H).

EXAMPLE 19

Preparation of 7-[(2', 6'-dinitro-4'-trifluoromethylphenyl)amino]-4,11,17,20,25,28-hexaoxa-1,14-diazatricyclo[12,8,8,0,5,10]-triaconta-5,7,9-triene.

A solution of 0.65 g of the amine obtained in Example 18 and 0.41 g of 4-chloro-3,5-dinitro benzotrifluoride in 22 ml of methanol are stirred with 0.13 g of sodium hydrogen carbonate under a nitrogen atmosphere and heated at reflux temperature for 20 hours. After cooling to ambient temperature, the solution is evaporated to dryness. The residue is dissolved in dichloromethane and passed through a column of alumina. The product is eluted with a mixture of 1% methanol in dichloromethane. The solution is evaporated to dryness, leaving a brilliant red powder. Yield 30%: IR 1511 $cm^{-1}$ and 1355 (aromatic C-$NO_2$). 3452 (secondary N-H): $^1$HNMR (CDCl$_3$) δ 8.42 (s, 1H), 8.38 (s, 1H), 6.88 (d, 1H), 6.78 (m, 1H), 6.67 (m, 1H), 4.1–4.25 (m, 4H), 3.65 (s, 8H), 3.4–3.6 (br m, 8H), 2.84 (m, 4H), 2.7 (m, 8H); FABMS 674 (M+H), 696 (M+Na).

What is claimed is:

1. An ionophore compound of an ion-recognizing system fused to a signal moiety through two heteroatoms having a non-bonded electron pair, having the formula:

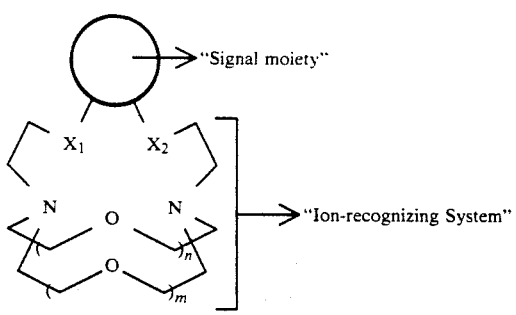

wherein:

said signal moiety is selected from the group consisting of unsubstituted and substituted coumarins, and wherein said ion-recognizing system is a three dimensional cryptand, wherein $X_1$, and $X_2$ of said cryptand are the same or different and are selected from the group consisting of S, p, N, O, and Se; and wherein the repeating units m and n are the same or different are each an integer of 0 to 12.

2. The inophore compound of claim 1 wherein $X_1$ and $X_2$ are the same and are O.

3. The ionophore compound of claim 2 wherein n is from 0 to 3 and m is about 0–5.

4. The ionophore compound of claim 3 wherein n is 2 and the signal moiety is a coumarin.

5. The inophore compound of claim 1 wherein the inophore compound corresponds to a formula selected from the group consisting of:

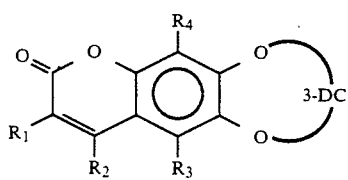

(a)

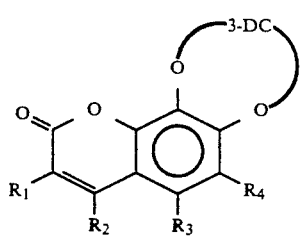

(b)

wherein $R_1$, $R_2$, $R_3$ and $R_4$ are the same or different and are N, hydroxyl, amino, alkyl, aromatic hydrocarbyl, fluoroalkyl, alkyloarbonyloxyl, carboxyl, alkoxyl, mercapto or alkylthio and 3-DC represents a 3 dimensional cryptand.

6. A compound having the following formula:

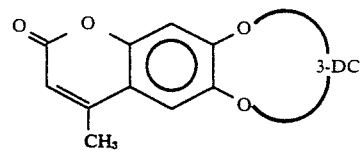

wherein 3-DC is a 3-dimensional cryptand.

7. The compound of claim 5 wherein $R_1$, $R_2$, $R_3$ and $R_4$ are the same or different and are selected from H and alkyl having 1 to 4 carbons.

8. The compound of claim 5 wherein $R_1$, $R_2$, $R_3$ and $R_4$ are the same or different and are selected from H or methyl or ethyl.

9. A compound according to claim 5 having the formula:

Structure 17

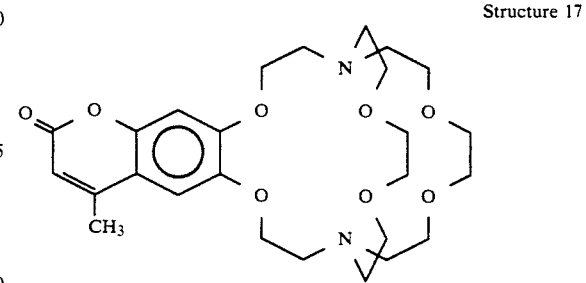

wherein said compound is a fluorogenic reagent selective for the detection of potassium ion.

10. A compound according to claim 5 having the formula:

Structure 18

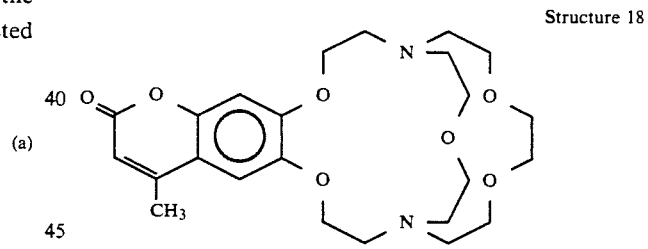

wherein said compound is a fluorogenic reagent for the detection of sodium ion.

11. A compound according to claim 5 having the formula:

Structure 19

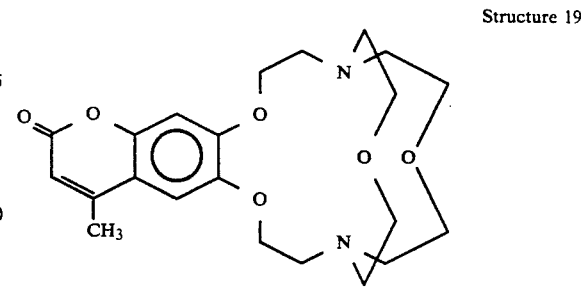

wherein said compound is a fluorogenic reagent for the detection of lithium ion.

* * * * *

UNITED STATES PATENT AND TRADEMARK OFFICE
CERTIFICATE OF CORRECTION

PATENT NO. : 5,162,525
DATED : November 10, 1992
INVENTOR(S) : D. Masilamani, et al.

It is certified that error appears in the above-identified patent and that said Letters Patent is hereby corrected as shown below:

The exact page and line numbers where the errors occurring the application file are:

Column 1, line 17, column 2, line 2, and column 9, line 10 change "in vivo" to --*in vivo*--.

Column 1, lines 17 - 18, change "in vitro" to --*in vitro*--.

Column 1, line 31, change "Reagents." to --Reagents,--.

Column 1, line 31, change ". 18" to --, 18--.

Column 1, lines 33 - 34, change "reagents." to --Reagents,--

Column 1, line 34, change "1984 121" to --1984, 121--.

Column 1, line 58, insert --,-- after "al.".

Column 1, line 59, change "*pp*" to --pp--.

Column 1, line 65, change "in situ" to --*in situ*--.

Column 2, line 8 insert --,-- after "pair".

Column 2, line 32, insert --,-- after "(O)".

Column 2, line 61, change "6.7- " to --6, 7- --.

Column 4, line 63, replace "nm." with -- nm,--.

Column 5, line 21, replace "345," with -- 3, 4, 5 --.

UNITED STATES PATENT AND TRADEMARK OFFICE
CERTIFICATE OF CORRECTION

PATENT NO. : 5,162,525

DATED : November 10, 1992

INVENTOR(S) : D. Masilamani, et al.

It is certified that error appears in the above-identified patent and that said Letters Patent is hereby corrected as shown below:

Column 5, line 48, replace "H. hydroxy, amine, alky," with -- H, hydroxy, amine, alkyl,--.

Column 7, line 22 replace "Thus,." with --Thus, --.

Column 7, line 31 replace "pure" with --Pure--.

Column 7, line 32, replace "49" with -- 49--.

Column 7, line 33, replace "ctyptands" with --cryptands --.

Column 8, line 14, replace "1.10-diaza-18-crown-6. 1.7-- - with --1,10-diaza-18-crown-6, 1,7- --.

Column 8, line 15, replace "1.10-" with --1,10- --.

Column 8, line 16, replace "1.16-" with --1,16- --.

Column 8, line 18, replace "de novo" with --*de novo*--.

Column 8, line 28, replace "(6.7-" with --(6,7- --.

Column 8, line 33, replace "1.10-" with --1,10- --.

Column 8, line 40, replace "Jun." with -- June --.

Column 10, line 28, insert --,-- before "the".

Column 10, line 33, replace "20" with --20--.

UNITED STATES PATENT AND TRADEMARK OFFICE
CERTIFICATE OF CORRECTION

PATENT NO. : 5,162,525

DATED : November 10, 1992

INVENTOR(S) : D. Masilamani, et al.

It is certified that error appears in the above-identified patent and that said Letters Patent is hereby corrected as shown below:

Column 10, line 68, replace "ions ionophores" with --ions. Ionphores"--.

Column 11, line 37, replace "in vivo" with -- *in vivo*--.

Column 12, line 63, replace " (6.7- " with -- (6,7- --

Column 13, line 46, replace "Jun." with -- June --.

Column 14, line 37, replace "ion, potassium" with --ion. Potassium --.

Column 14, line 45, replace "With" with -- with --.

Column 15, line 6, replace "12,5" with --12.5--.

Column 15, line 50, replace "compound Yield" with -- compound. Yield --.

Column 15, line 58, replace "ln" with --in--.

Column 16, line 8, replace "(5.450), 287 (1.690)" with -- (5,450), 287 (1,690 )--

Column 16, line 16, replace "1.7-" with -- 1,7- --.

Column 16, line 23, replace "4,giving" with --4, giving--.

Column 16, lines 43 - 44, replace "(3.920), 339 (8.600)" with -- (3,920), 339 (8,600)--.

UNITED STATES PATENT AND TRADEMARK OFFICE
CERTIFICATE OF CORRECTION

PATENT NO. : 5,162,525

DATED : November 10, 1992

INVENTOR(S) : D. Masilamani, et al.

It is certified that error appears in the above-identified patent and that said Letters Patent is hereby corrected as shown below:

Column 16, line 48, replace "6.7-" with -- 6,7- --.

Column 16, line 51, replace "1.7-" with -- 1,7- --.

Column 16, line 52, replace "Jun." with --June --.

Column 16, line 65, replace "H)." with -- H),--.

Column 17, line 6, replace "$10^3 1\ 3$ M" with -- $10^{-3}$ M --.

Column 17, line 11, replace "With" with --with--.

Column 18, line 5, replace "fluoroqenic" with --fluorogenic--.

Column 18, line 9, replace "Water" with --water--.

Column 18, line 37, replace "postassium" with --potassium--.

Column 19, line 11, replace "Whereas" with --whereas--.

Column 19, line 49, replace "18No." with --18 No. --

Column 20, line 3, replace "$\delta 7.83$" with -- $\delta\ 7.83$ --.

Column 20, line 21, insert --:-- after "%".

Column 20, line 31, replace "[12,8,8,0,5,10]" with -- (12,8,8,0,5,10)--.

Claim 1, column 21, second line from bottom of claim, replace "p" with --P--

UNITED STATES PATENT AND TRADEMARK OFFICE
CERTIFICATE OF CORRECTION

PATENT NO. : 5,162,525

DATED : November 10, 1992

INVENTOR(S) : D. Masilamani, et al.

It is certified that error appears in the above-indentified patent and that said Letters Patent is hereby corrected as shown below:

Claim 2, column 21, first line of claim, replace "inophore" with --ionophore--.

Claim 5, column 21, third line from bottom of claim, replace "N" with --H--.

Claim 5, column 21, second line from bottom of claim, replace "alkyloaronyloxyl," with --alkylcarbonyloxyl,--.

Claim 5, column 21, insert --, wherein $R_1$ to $R_4$ are selected as to not substantially interfere with the ability of the ionophore to exhibit an optical change upon recognizing an ion being tested for,-- after "alkylthio".

Signed and Sealed this

Fourth Day of July, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,162,525                                   Page 1 of 5
DATED      : November 10, 1992
INVENTOR(S): D. Masilamani, et al It is certified that error appears in the above-indentified patent and that said Letters Patent is hereby corrected as shown below:

Column 1, line 17, column 2, line 2, and column 9, line 10 change "in vivo" to --*in vivo*--.

Column 1, lines 17 - 18, change "in vitro" to --*in vitro*--.

Column 1, line 31, change "Reagents." to --Reagents,--.

Column 1, line 31, change ". 18" to -- 18--.

Column 1, lines 33 - 34, change "reagents." to --Reagents,--

Column 1, line 34, change "1984 121" to --1984 121--

Column 1, line 58, insert --,-- after "al.".

Column 1, line 59, change "*pp*" to --pp--.

Column 1, line 65, change "in situ" to --*in situ*--.

Column 2, line 8 insert --,-- after "pair".

Column 2, line 32, insert --,-- after "(O)".

Column 2, line 61, change "6.7- " to --6, 7- --.

Column 4, line 63, replace "nm." with -- nm,--

Column 5, line 21, replace "345," with -- 3, 4, 5 --.

UNITED STATES PATENT AND TRADEMARK OFFICE
CERTIFICATE OF CORRECTION

PATENT NO. : 5,162,525
DATED : November 10, 1992
INVENTOR(S) : D. Masilamani, et al It is certified that error appears in the above-indentified patent and that said Letters Patent is hereby corrected as shown below:

Column 5, line 48, replace "H. hydroxy, amine, alky," with -- H, hydroxy, amine, alkyl,--.

Column 7, line 22 replace "Thus,." with --Thus, --.

Column 7, line 31 replace "pure" with --Pure--.

Column 7, line 32, replace "49" with -- 49--.

Column 7, line 33, replace "ctyptands" with --cryptands --.

Column 8, line 14, replace "1.10-diaza-18-crown-6. 1.7-- - with --1,10-diaza-18-crown-6, 1,7- --.

Column 8, line 15, replace "1.10-" with --1,10- --.

Column 8, line 16, replace "1.16-" with --1,16- --.

Column 8, line 18, replace "de novo" with --*de novo*--.

Column 8, line 28, replace "(6.7-" with --(6,7- --.

Column 8, line 33, replace "1.10-" with --1,10- --.

Column 8, line 40, replace "Jun." with -- June --.

Column 10, line 28, insert --,-- before "the".

Column 10, line 33, replace "20" with --20--.

UNITED STATES PATENT AND TRADEMARK OFFICE
CERTIFICATE OF CORRECTION

PATENT NO. : 5,162,525
DATED : November 10, 1992
INVENTOR(S) : D. Masilamani, et al Page 3 of 5

It is certified that error appears in the above-indentified patent and that said Letters Patent is hereby corrected as shown below:

Column 10, line 68, replace "ions ionophores" with --ions. Ionphores" --

Column 11, line 37, replace "in vivo" with -- *in vivo*-

Column 12, line 63, replace " (6.7- " with -- (6,7- -

Column 13, line 46, replace "Jun." with -- June --.

Column 14, line 37, replace "ion, potassium" with --ion. Potassium --.

Column 14, line 45, replace "With" with -- with --.

Column 15, line 6, replace "12,5" with --12.5--.

Column 15, line 50, replace "compound Yield" with -- compound. Yield --.

Column 15, line 58, replace "ln" with --in--.

Column 16, line 8, replace "(5.450), 287 (1.690)" with -- (5,450), 287 (1,690)

Column 16, line 16, replace "1.7-" with -- 1,7- --.

Column 16, line 23, replace "4,giving" with --4, giving--.

Column 16, lines 43 - 44, replace "(3.920), 339 (8.600)" with -- (3,920), 339 (8,600)--.

UNITED STATES PATENT AND TRADEMARK OFFICE
CERTIFICATE OF CORRECTION

PATENT NO. : 5,162,525  
DATED : November 10, 1992  
INVENTOR(S) : D. Masilamani, et al Page 4 of 5

It is certified that error appears in the above-indentified patent and that said Letters Patent is hereby corrected as shown below:

Column 16, line 48, replace "6.7-" with -- 6,7- --.

Column 16, line 51, replace "1.7-" with -- 1,7- --.

Column 16, line 52, replace "Jun." with --June --.

Column 16, line 65, replace "H)." with -- H),--.

Column 17, line 6, replace "$10^{3 1 3}$ M" with -- $10^{-3}$ M --.

Column 17, line 11, replace "With" with --with--

Column 18, line 5, replace "fluoroqenic" with --fluorogenic--.

Column 18, line 9, replace "Water" with --water-

Column 18, line 37, replace "postassium" with --potassium--.

Column 19, line 11, replace "Whereas" with --whereas--.

Column 19, line 49, replace ".8No." with --.8 No. --

Column 20, line 3, replace "$\delta 7.83$" with -- $\delta$ 7.83 --.

Column 20, line 21, insert --:-- after "%".

Column 20, line 31, replace "[12,8,8,0,5,10]" with -- (12,8,8,0,5,10)--.

Claim 1, column 21, second line from bottom of claim, replace "p" with --P--

UNITED STATES PATENT AND TRADEMARK OFFICE
CERTIFICATE OF CORRECTION

PATENT NO.   : 5,162,525
DATED        : November 10, 1992
INVENTOR(S)  : D. Masilamani, et al It is certified that error appears in the above-indentified patent and that said Letters Patent is hereby corrected as shown below:

Claim 2, column 21, first line of claim, replace "inophore" with --ionophore--

Claim 5, column 21, lines 1 and 2 of claim, replace "inophore" with --ionophore--.

Claim 5, column 21, third line from bottom of claim, replace "N" with --H-

Claim 5, column 21, second line from bottom of claim, replace "alkyloarbonyloxyl," with --alkylcarbonyloxyl,--.

Signed and Sealed this

Nineteenth Day of December, 1995

Attest:

BRUCE LEHMAN

*Attesting Officer*     *Commissioner of Patents and Trademarks*